United States Patent [19]

Kelen et al.

[11] Patent Number: 5,109,862
[45] Date of Patent: May 5, 1992

[54] METHOD AND APPARATUS FOR SPECTRAL ANALYSIS OF ELECTROCARDIOGRAPHIC SIGNALS

[75] Inventors: George J. Kelen, Staten Island, N.Y.; Raphael Henkin, Monarch Beach, Calif.

[73] Assignee: Del Mar Avionics, Irvine, Calif.

[21] Appl. No.: 658,505

[22] Filed: Feb. 21, 1991

Related U.S. Application Data

[63] Continuation of Ser. No. 496,976, Mar. 19, 1990, abandoned.

[51] Int. Cl.⁵ .............................................. A61B 5/048
[52] U.S. Cl. .................................. 128/702; 364/413.06
[58] Field of Search ......................... 128/696, 702–705; 364/413.06

[56] References Cited

U.S. PATENT DOCUMENTS

| | | | |
|---|---|---|---|
| 4,630,204 | 12/1986 | Mortara | 128/696 |
| 4,802,491 | 2/1989 | Cohgn et al. | 128/702 |
| 4,924,875 | 5/1990 | Chamoun | 128/696 |

Primary Examiner—William E. Kamm
Attorney, Agent, or Firm—William Chapin; J. D. Leimbach

[57] ABSTRACT

A frequency domain signal processing and analysis method and apparatus displays, plots and makes measurements upon electrocardiographic signals (ECG) recorded from the body surface. Both the graphic plots and the numeric parameters measured reveal abnormalities of electrical conduction within the heart thought to be important in the identification of patients at risk of serious disturbances of heart rhythm including sudden death. The invention employs Fourier analysis of short overlapping segments of ECG signal to create a three dimensional map ("spectrocardiogram") whose axes are time, fequency and power thus disclosing changes in the frequency content of the ECG signal over short intervals of time. In additoin to the Fourier analysis itself, the method and apparatus provides a wide choice of user-selectable signal pre-processing, post-processing, display and plotting options as well as performing custom mathematical computations upon the Fourier spectra to distinguish and quantify visually apparent differences between normal and abnormal spectrocardiograms.

59 Claims, 17 Drawing Sheets

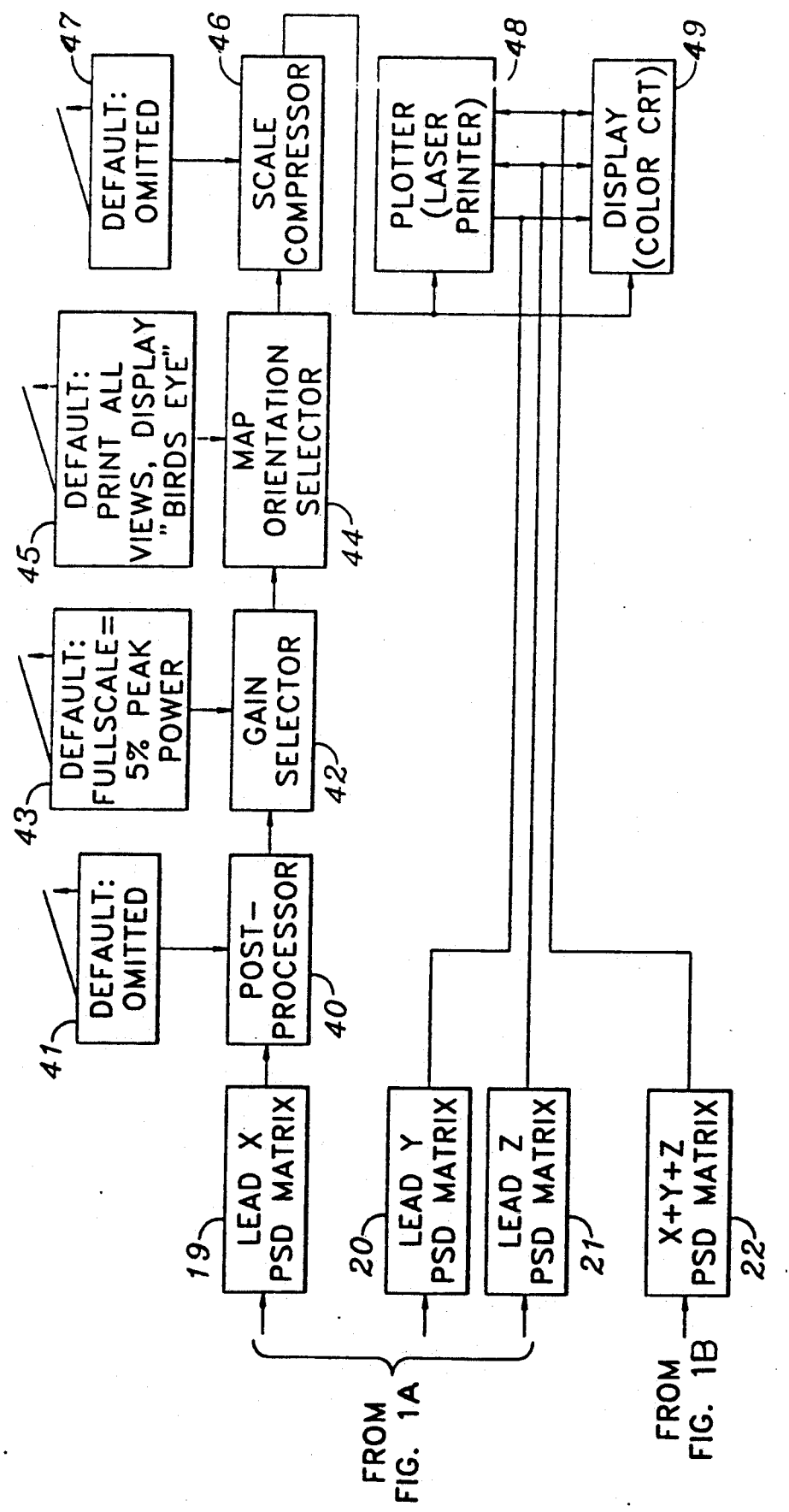
FIG. IC

LEAD X

LEAD X

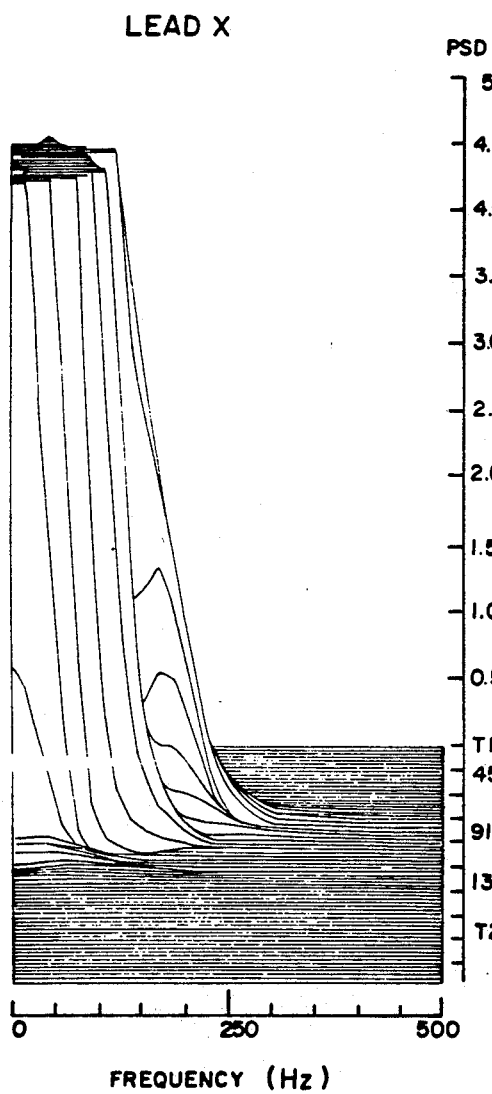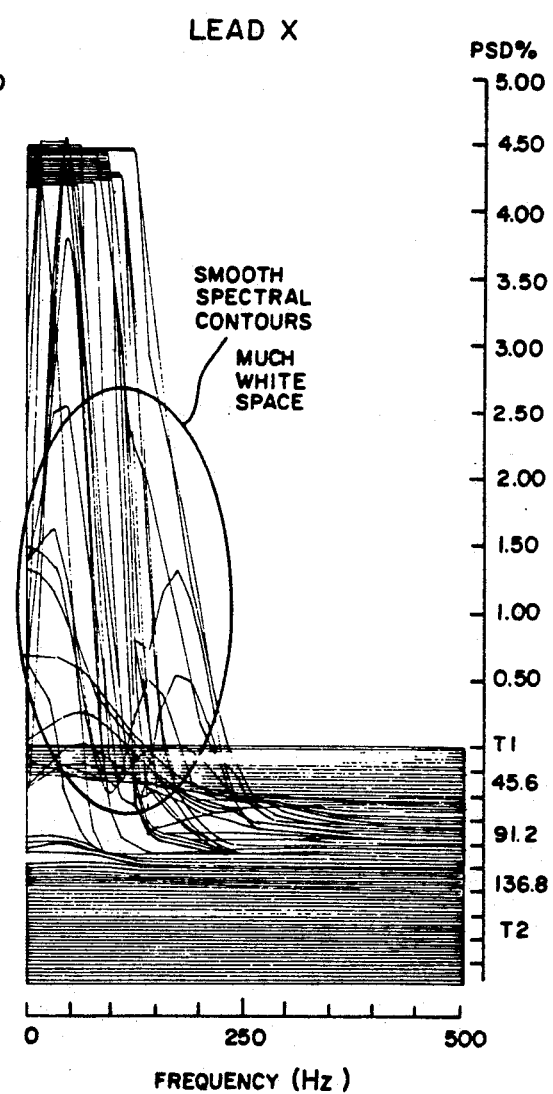
FIG. 3E LEAD X
FIG. 3F LEAD X

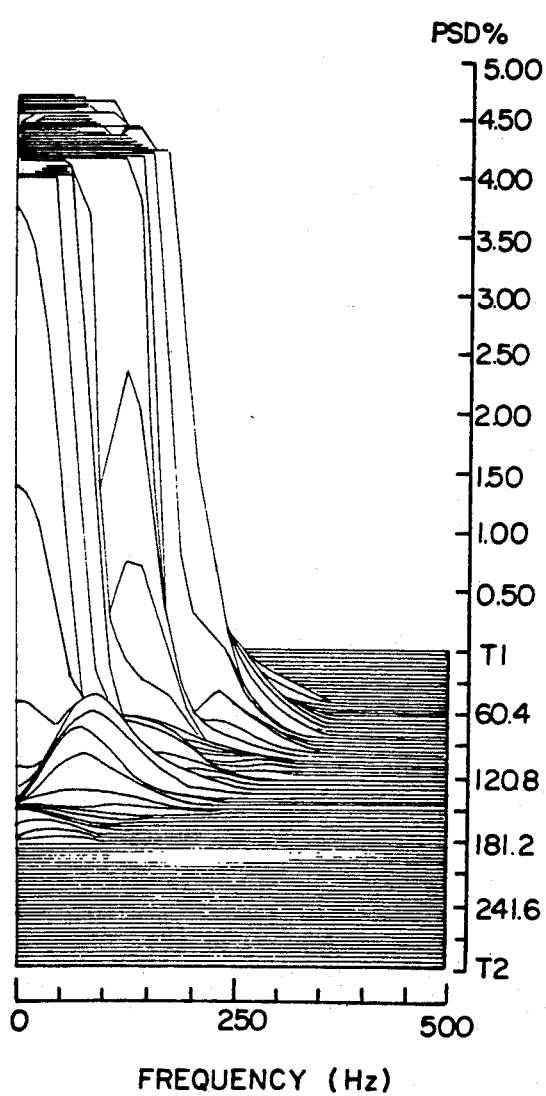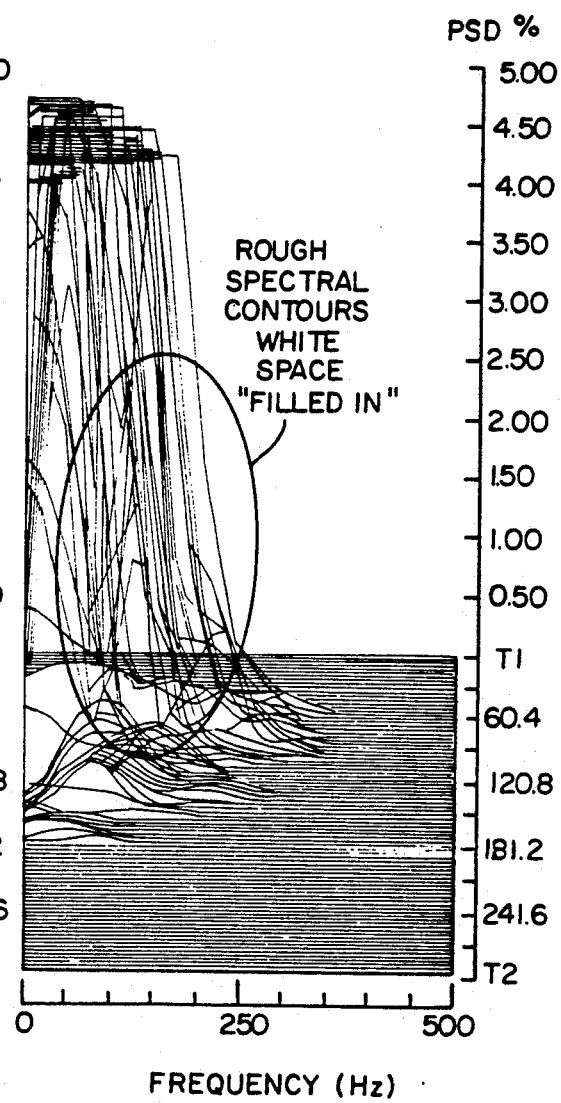
FIG. 4E LEAD X
FIG. 4F LEAD X

FIG. 5

"FALSE POSITIVE" HEALTHY VOLUNTEER

| PATIENT: | | REPORT NO.: | | BEATS AVERAGED: | 402 |
|---|---|---|---|---|---|
| AGE: | SEX: | REPORT DATE: | | SAMPLING FREQUENCY: | 1000 HZ |
| INDICATION: | | TEST DATE: | 11/16/87 | FILE NAME: | BECKERB.R00 |
| PHYSICIAN: | | SAMPLE TIME: | 14:43 | | |
| MEDICATION: | | | | | |
| COMMENT: | | | | | |

SPECTROCARDIOGRAM™     PARAMETERS:
TIME SLICE DURATION:                24.0 MSEC
TIME SLICE STEP INTERVAL:            2.0 MSEC
SIGNAL PRECONDITIONING:            VELOCITY
DC OFFSET SUBTRACTION:           PRE-WINDOW
FFT POINTS:                               64
WINDOW:                       BLACKMAN-HARRIS

LEAD X
TOTAL QRS DURATION: (MSEC) 92.0

LOW POWER TERMINAL QRS REGION

PSD40:                    (MSEC) 18.0
HFQRS DURATION:                  134.9
HF BIAXIAL PEAKS:                    3
HF FREQUENCY AXIS PEAKS:             8
HF TEMPORAL AXIS PEAKS:             10
LF BIAXIAL PEAKS:                    0
LF FREQUENCY AXIS PEAKS:             0
LF TEMPORAL AXIS PEAKS:              0
SPECTRAL TURBULANCE:                 8
LATE POTENTIAL DURATION:          13.9

HIGH POWER MAIN QRS REGION

REGION DURATION: (MSEC) 66.0
HF BIAXIAL PEAKS:                    4
HF FREQUENCY AXIS PEAKS:            53
HF TEMPORAL AXIS PEAKS:             96
LF BIAXIAL PEAKS:                    0
LF FREQUENCY AXIS PEAKS:             0
LF TEMPORAL AXIS PEAKS:              0
SPECTRAL TURBULANCE:                 7
LATE POTENTIAL DURATION:          11.5

LEAD Y
TOTAL QRS DURATION: (MSEC) 124.0

LOW POWER TERMINAL QRS REGION

PSD40:                    (MSEC) 52.0
HFQRS DURATION:                    0.8
HF BIAXIAL PEAKS:                    4
HF FREQUENCY AXIS PEAKS:            23
HF TEMPORAL AXIS PEAKS:             24
LF BIAXIAL PEAKS:                    0
LF FREQUENCY AXIS PEAKS:             0
LF TEMPORAL AXIS PEAKS:              0
SPECTRAL TURBULANCE:                11
LATE POTENTIAL DURATION:          17.9

HIGH POWER MAIN QRS REGION

REGION DURATION: (MSEC) 66.0
HF BIAXIAL PEAKS:                    8
HF FREQUENCY AXIS PEAKS:            58
HF TEMPORAL AXIS PEAKS:             107
LF BIAXIAL PEAKS:                    0
LF FREQUENCY AXIS PEAKS:             0
LF TEMPORAL AXIS PEAKS:              0
SPECTRAL TURBULANCE:                12
LATE POTENTIAL DURATION:          20.7

LEAD Z
TOTAL QRS DURATION: (MSEC) 130.0

LOW POWER TERMINAL QRS REGION

PSD40:                    (MSEC) 52.0
HFQRS DURATION:                    1.5
HF BIAXIAL PEAKS:                    3
HF FREQUENCY AXIS PEAKS:            19
HF TEMPORAL AXIS PEAKS:              30
LF BIAXIAL PEAKS:                    0
LF FREQUENCY AXIS PEAKS:             0
LF TEMPORAL AXIS PEAKS:              0
SPECTRAL TURBULANCE:                10
LATE POTENTIAL DURATION:          16.0

HIGH POWER MAIN QRS REGION

REGION DURATION: (MSEC) 78.0
HF BIAXIAL PEAKS:                    10
HF FREQUENCY AXIS PEAKS:            68
HF TEMPORAL AXIS PEAKS:             118
LF BIAXIAL PEAKS:                    0
LF FREQUENCY AXIS PEAKS:             0
LF TEMPORAL AXIS PEAKS:              0
SPECTRAL TURBULANCE:                12
LATE POTENTIAL DURATION:          21.0

X + Y + Z
TOTAL QRS DURATION: (MSEC) 122.0

LOW POWER TERMINAL QRS REGION

PSD40:                    (MSEC) 46.0
HFQRS DURATION:                    1.4
HF BIAXIAL PEAKS:                    5
HF FREQUENCY AXIS PEAKS:            23
HF TEMPORAL AXIS PEAKS:             19
LF BIAXIAL PEAKS:                    0
LF FREQUENCY AXIS PEAKS:             0
LF TEMPORAL AXIS PEAKS:              0
SPECTRAL TURBULANCE:                 7
LATE POTENTIAL DURATION:           8.0

HIGH POWER MAIN QRS REGION

REGION DURATION: (MSEC) 72.0
HF BIAXIAL PEAKS:                    4
HF FREQUENCY AXIS PEAKS:            54
HF TEMPORAL AXIS PEAKS:             100
LF BIAXIAL PEAKS:                    0
LF FREQUENCY AXIS PEAKS:             0
LF TEMPORAL AXIS PEAKS:              0
SPECTRAL TURBULANCE:                 6
LATE POTENTIAL DURATION:           9.1

INTERPRETATION:

FIGURE 6

"TRUE POSITIVE" PATIENT AT RISK

| | | |
|---|---|---|
| Patient: | Report No.: 0687 | Beats Averaged: 675 |
| Age:  Sex: | Report Date: | Sampling Frequency: 1000 Hz |
| Indication: | Test Date: 29.08.08 | File Name: berry.r00 |
| Physician: | Sample Time: 05:15 | |
| Medication: | | |
| Comment: | | |

LEAD X
Total QRS Duration: 166.0 msec

LOW POWER TERMINAL QRS REGION
PSD40: 70.0 msec
HFQRS Duration: 1.8
HF Biaxial Peaks: 5
HF Frequency Axis Peaks: 40
HF Temporal Axis Peaks: 69
LF Biaxial Peaks: 0
LF Frequency Axis Peaks: 0
LF Temporal Axis Peaks: 0
Spectral Turbulence: 18
Late Potential Duration: 33.0

HIGH POWER MAIN QR REGION
Region Duration: 96.0 msec
HF Biaxial Peaks: 12
HF Frequency Axis Peaks: 85
HF Temporal Axis Peaks: 155
LF Biaxial Peaks: 0
LF Frequency Axis Peaks: 0
LF Temporal Axis Peaks: 0
Spectral Turbulence: 16
Late Potential Duration: 25.9

LEAD Y
Total QRS Duration: 170.0 msec

LOW POWER TERMINAL QRS REGION
PSD40: 72.0 msec
HFQRS Duration: 0.6
HF Biaxial Peaks: 7
HF Frequency Axis Peaks: 41
HF Temporal Axis Peaks: 59
LF Biaxial Peaks: 0
LF Frequency Axis Peaks: 0
LF Temporal Axis Peaks: 0
Spectral Turbulence: 26
Late Potential Duration: 47.0

HIGH POWER MAIN QRS REGION
Region Duration: 94.0 msec
HF Biaxial Peaks: 15
HF Frequency Axis Peaks: 76
HF Temporal Axis Peaks: 145
LF Biaxial Peaks: 0
LF Frequency Axis Peaks: 0
LF Temporal Axis Peaks: 0
Spectral Turbulence: 24
Late Potential Duration: 49.2

LEAD Z
Total QRS Duration: 140.0 msec

LOW POWER TERMINAL QRS REGION
PSD40: 44.0 msec
HFQRS Duration: 3.0
HF Biaxial Peaks: 5
HF Frequency Axis Peaks: 28
HF Temporal Axis Peaks: 56
LF Biaxial Peaks: 0
LF Frequency Axis Peaks: 0
LF Temporal Axis Peaks: 0
Spectral Turbulence: 12
Late Potential Duration: 18.3

HIGH POWER MAIN QRS REGION
Region Duration: 92.0 msec
HF Biaxial Peaks: 10
HF Frequency Axis Peaks: 70
HF Temporal Axis Peaks: 132
LF Biaxial Peaks: 0
LF Frequency Axis Peaks: 0
LF Temporal Axis Peaks: 0
Spectral Turbulence: 20
Late Potential Duration: 26.9

X + Y + Z
Total QRS Duration: 164.0 msec

LOW POWER TERMINAL QRS REGION
PSD40: 68.0 msec
HFQRS Duration: 1.1
HF Biaxial Peaks: 5
HF Frequency Axis Peaks: 35
HF Temporal Axis Peaks: 56
LF Biaxial Peaks: 0
LF Frequency Axis Peaks: 0
LF Temporal Axis Peaks: 0
Spectral Turbulence: 13
Late Potential Duration: 21.0

HIGH POWER MAIN QRS REGION
Region Duration: 96.0 msec
HF Biaxial Peaks: 9
HF Frequency Axis Peaks: 71
HF Temporal Axis Peaks: 138
LF Biaxial Peaks: 0
LF Frequency Axis Peaks: 0
LF Temporal Axis Peaks: 0
Spectral Turbulence: 6
Late Potential Duration: 11.6

Spectrocardiogram™
Time slice duration: 24.0 msec.
Time slice step interval: 2.0 msec.
Signal preconditioning: Velocity
DC Offset subtraction: Pre-Window
FFT Points: 64
Window: Blackman-Harris Parameters:

INTERPRETATION:

FIG. 7

Spectrocardiogram is a trademark of Del Mar Avionics

LEAD Z

SUM (X+Y+Z)

EXAMPLE PSD MATRIX TABLE,
ONE FOR EACH LEAD, AS
WELL AS X+Y+Z

K SLICES, N POINT FFT, $F_0$ IS FUNDAMENTAL
$F_X$ IS $X^{TH}$ HARMONIC

| SLICE # | $F_0$ | $F_1$ | $F_2$ | ... | $F_{\frac{N}{2}-1}$ | $F_{\frac{N}{2}}$ | $\sum_{F_0}^{F_{N/2}}$ |
|---|---|---|---|---|---|---|---|
| 1 | PSD | PSD | PSD | ... | | | |
| 2 | | | | ... | | | |
| 3 | | | | ... | | | |
| ⋮ | ⋮ | ⋮ | ⋮ | ⋮ | ⋮ | ⋮ | ⋮ |
| K−1 | | | | ... | | | |
| K | | | | ... | | | |
| "AVERAGE" SLICE OF LOW POWER REGION | | | | ... | PSD | PSD | PSD |

FIG. 10

METHOD AND APPARATUS FOR SPECTRAL ANALYSIS OF ELECTROCARDIOGRAPHIC SIGNALS

This is a continuation of application Ser. No. 07/496,976, filed Mar. 19, 1990, now abandoned.

BACKGROUND OF THE INVENTION

A. Field of the Invention

This invention relates to methods and devices for analysis of the electrical activity of the heart (Electrocardiography) and more particularly to the field known as High Resolution Electrocardiography, which is concerned with detecting abnormalities not apparent on conventional electrocardiograms. The specific and major purpose intended for the present invention is the clinical evaluation of medical patients for risk of life-threatening arrhythmias of the heart. However, both the method and apparatus are potentially suitable for research into and diagnosis of a wide variety of other disorders of cardiac electrical activity, and the analysis of other bio-electrical signals such as those recorded on an Electroencephalogram (EEG).

B. Description of the Background Art

In order to fully comprehend the purpose and method of the present invention, it is necessary to be familiar with certain standard physiological and electrocardiographic (ECG) nomenclature. Relevant portions of that nomenclature are briefly summarized here, for the benefit of the reader not conversant with medical terminology.

The pumping action of the normal heart results from the orderly contraction of millions of individual muscle cells. Each heart beat is initiated by the spontaneous periodic activity of certain specialized cells of a structure known as the sino-atrial node. Activation of heart muscle cells is initiated by an electrical pacing signal generated in the sino-atrial node and propagated by specialized tissues known collectively as "the conducting system" of the heart. At the cellular level, the process of activation is known as "depolarization" since it involves transient changes in the electrical potential across the cell membrane mediated by the passage of ions The process of recovery to the normal "resting" state is referred to as "repolarization."

The spread of the wavefront of electrical depolarization through the atria (or "primer pumping chambers") of the heart gives rise to the deflection on the electrocardiogram known as the "P" wave. Contraction of the main cardiac pumping chambers, or ventricles, is associated with a biphasic or multiphasic deflection of the ECG waveform known as the "QRS complex." Spread of the wavefront of electrical recovery (repolarization) through the ventricles gives rise to the "T" wave of the ECG. The time interval between the end of the QRS complex and the T Wave, referred to as the "ST segment" is normally free from electrical activity, but may harbor small amplitude signals known as "late potentials" which extend out beyond the end of the QRS complex (viewed at ordinary magnification) into the ST segment. All of the components of ECG waveforms result from the synchronous spread of electrical signals associated with the activation or recovery of individual cardiac cells, across millions of such cells.

Over 50,000 people die annually in the USA of unexpected or sudden cardiac death, almost always from a catastrophic failure of normal electrical conduction within the heart known as ventricular fibrillation. Instead of the normal orderly and synchronous contraction of the heart muscle cells necessary for pumping of blood to occur, individual muscle fibers contract in a random and totally disorganized fashion This arrhythmia (abnormal cardiac rhythm) frequently occurs in association with a myocardial infarction ("heart attack") either within the first minutes, hours, or sometimes months to years later, but is also the final common pathway for almost all forms of death from cardiac causes. Ventricular fibrillation is a terminal event because no blood at all is pumped and vital organs such as the brain die from lack of oxygen within minutes unless either the rhythm is corrected ("defibrillation") or the circulation is artificially supported by some other means such as CPR or cardio-pulmonary bypass ("heart-lung machine").

A frequent immediate predecessor to ventricular fibrillation is another arrhythmia known as ventricular tachycardia ("VT") during which, although some blood is pumped, the heart rate is usually much more rapid than the maximum rate at which the heart may function effectively as an efficient pump. This excessive heart rate frequently results in symptoms such as loss of consciousness or lightheadedness. VT may spontaneously revert to a more normal heart rhythm ("non-sustained") or be prolonged for more than 30 seconds ("sustained"), in which latter case the development of symptoms or progression to ventricular fibrillation is much more common.

Despite the existence of a wide variety of more or less successful treatments such as drug therapy, surgery or implantable defibrillators for the prevention or correction of ventricular arrhythmias, their use is not without risk or expense of its own. Classical electrocardiography as practiced for several decades is unfortunately very poor at predicting who is likely to suffer such an event. Although it is known that increased risk is associated with certain states such as a severely damaged or dilated left ventricle (main pumping chamber of the heart), there remains an urgent need for a means of delineating those patients at significant risk, who might truly benefit from aggressive therapies, from amongst the vast majority of potential candidates in whom the risk of life threatening arrhythmia is low and for whom aggressive (or expensive) therapies may actually do more harm than good. Such an arrhythmia risk screening test should preferably be "non-invasive," i.e., not require breaking of the skin surface and free from risk and discomfort to the patient.

The most reliable method currently available for predicting likelihood of development of a lethal arrhythmia is a diagnostic procedure called "electrophysiological study" (EP) during which slender wires ("pacing catheters") are introduced through the skin into a large vein and advanced under X-ray guidance into the heart chambers themselves. Using a device attached to the wires, which generates electrical impulses similar to those produced by a pacemaker, the interior surface of the heart is subjected to electrical stimulation pulses in an attempt to induce VT. If it proves possible to induce ventricular tachycardia which is " (of one shape or type) and "sustained" (not spontaneously terminating) the patient is deemed to be much more likely to spontaneously develop a lethal rhythm disorder. Unfortunately, EP study is invasive, requires admitting the patient to a hospital, is often distressing to the patient who may need to be defibrillated out of a successfully induced arrhythmia, and is time, labor and cost intensive.

Among available non-invasive arrhythmia risk assessment techniques, so-called "late potential analysis" has received most attention both in the literature and commercially. The patents of Simson, U.S. Pat. No. 4,422,459, Dec. 27, 1983, Netravali, U.S. Pat No. 4,458,691, Jul. 10, 1984, and Strick, U.S. Pat. No. 4,492,235, Jan. 8, 1985, teach a method currently in widespread use on real-time ECGs. Many variants of the method have been advocated in the medical literature. Late potentials are signals of very low amplitude (less than 40 uV versus about 1 mV for the main ECG signal proper) and thus require employment of a special noise reduction technique known as "signal averaging" for them to be discernible above the background noise. Their presence beyond the end of the normal QRS complex is about 70-80% predictive for inducibility of sustained monomorphic VT at EP study and hence development of a serious spontaneous ventricular arrhythmia. However, late potential analysis cannot be used at all in the presence of certain relatively common types of ECG abnormality, and its specificity and sensitivity leave much to be desired.

The method of Simson teaches identification of late potentials by analysis in the time domain only, without any attempt to explicitly analyze their frequency, or spectral content. Bipolar ECG signals from three orthogonal surface leads are bidirectionally filtered and then algebraically summed into a single "vector magnitude" upon which certain characteristics of the terminal QRS signal are then measured. Late potentials are deemed to be present or absent depending upon the duration and amplitude of the terminal QRS region. As already noted, late potentials are not infrequently found (by time domain techniques) in perfectly normal, healthy individuals. The present invention teaches among other things, a novel method of distinguishing such "false positive" late potentials from those associated with serious arrhythmia risk, based upon frequency spectra, or their "spectrocardiographic" features.

In U.S. Pat. No. 4,680,708, Jul. 14, 1987, Ambos, Cain & Sobel claim a frequency domain technique for late potential identification using Fourier analysis of a single, relatively long segment of ECG signal positioned over the terminal QRS region. Abnormality is allegedly characterized by presence of secondary high frequency peaks and an excess ratio of high frequencies to low frequencies.

In U.S. Pat. No. 4,883,065, one of the present inventors, Kelen, disclosed a novel system for the analysis of late potentials from long-term recordings of ECGs made on an ambulatory monitor, e.g., a Holter monitor.

The present invention teaches spectral mapping of multiple overlapping ECG signal segments, spanning the whole QRS complex, with abnormality recognizable by visual features of three dimensional maps and computed parameters not disclosed or suggested by Cain or any other prior art known by the present inventors. The novel method and apparatus of diagnosis via spectral feature analysis used in the present invention is applicable to the analysis of ECG signals recorded on Holter monitor tapes, as well as in real time.

OBJECTS OF THE INVENTION

An object of the present invention is to provide an ECG analysis method and apparatus by which it is possible to identify patients at significant risk of experiencing a serious ventricular arrhythmia.

Another object of the invention is to provide a ventricular arrhythmia risk analysis method and apparatus that does not require invasion of the human body, puncturing of the patient's skin, admission to hospital, or significant risk, pain or discomfort to the patient.

Another object of the invention is to provide a method and apparatus for frequency analysis of ECG signals that can distinguish late potentials that are likely to be associated with serious arrhythmia risk from "false positives" occurring in normal subjects.

Another object of the invention is to provide a method and apparatus for the calculation of numeric parameters which may be useful in distinguishing normal from abnormal heart function, in addition to the graphic display and hard copy generation of the spectral maps from which the numerical calculations are derived, thus providing both visual qualitative and numerical quantitative methods for classification of recordings.

Another object of the invention is to provide a frequency analysis method and apparatus which in its standard default mode of operation performs, upon issue of a single command, analysis according to a fixed predefined stepwise signal processing protocol that results without further operator intervention in the generation of visual plots and a numeric report suitable for ventricular arrhythmia risk prediction. In this default routine mode of operation, the invention should be suitable for use by a technician.

Another object of the invention is to provide a frequency analysis method and apparatus having an operator interactive mode of operation whereby the individual steps of the analysis protocol can be customized from a menu, with sufficient flexibility and convenience so as to be suitable for use by researchers seeking to identify improved means of making electrocardiographic diagnoses based upon the visualization and measurement of the frequency characteristics of ECG signals as they change with time.

Various other objects and advantages of the present invention, and its most novel features, will become apparent to those skilled in the art by reading the accompanying specification and claims and studying the figures exemplifying the results of applying the invention to normal and abnormal subjects.

It is to be understood that although the invention disclosed herein is fully capable of achieving the objects and providing the advantages described, the description of the invention contained herein is merely illustrative of the preferred embodiments. Accordingly, we do not intend that the scope of our exclusive rights and privileges in the invention be limited to the details of the embodiments described. We do intend that reasonable equivalents, adaptations and modifications of the various embodiments and alternate forms of the present invention which are described herein be included within the scope of this invention as particularly pointed out by the appended claims.

SUMMARY OF THE INVENTION

Briefly stated, the present invention comprehends a method and apparatus for performing frequency analysis upon relatively short, stepped but overlapping segments of ECG signals from one or more channels, in combination with pre-processing and post-processing steps appropriate to the intended purpose, to generate three dimensional maps reflecting the amplitude and time course of the various frequency components, or Fourier spectra, of said ECG signals. From the same frequency component or spectral data used to generate the maps, calculations are made of numeric parameters which quantify visually apparent morphological features of the maps, such as contour smoothness and number and position of frequency peaks. The three-dimensional maps, which may be plotted in several different orientations, are combined with a printout of the numeric parameters to generate a report from which both visual morphologic and quantitative assessments of abnormality can be made.

BRIEF DESCRIPTION OF THE FIGURES

FIGS. 1A-1C comprise a block diagram of one embodiment of the apparatus for spectral analysis of electrocardiographic signals according to the present invention.

FIGS. 2A-2F through 4A-4F are spectral ECG plots generated by the apparatus.

FIGS. 5 through 7 are printed reports generated by the apparatus of FIG. 1 corresponding to the spectral plots of FIGS. 2 through 4, respectively.

FIGS. 8A-8F and 9A-9F are spectral ECG plots generated by the apparatus of FIG. 1, in which the default analysis protocol of the apparatus has been modified by operator intervention.

FIG. 10 is a schematic view of a table of intermediate values calculated by the apparatus of FIG. 1.

DETAILED DESCRIPTION OF THE INVENTION

FIG. 1 is a block diagram of a basic embodiment of an apparatus for the spectral analysis of electrocardiographic signals according to the present invention. Much of the apparatus of FIG. 1 can be implemented as software modules running on a microprocessor system.

Those skilled in the art will recognize that the apparatus may be implemented with alternate means which perform the functions indicated for the various blocks of FIG. 1.

Figure 1A:
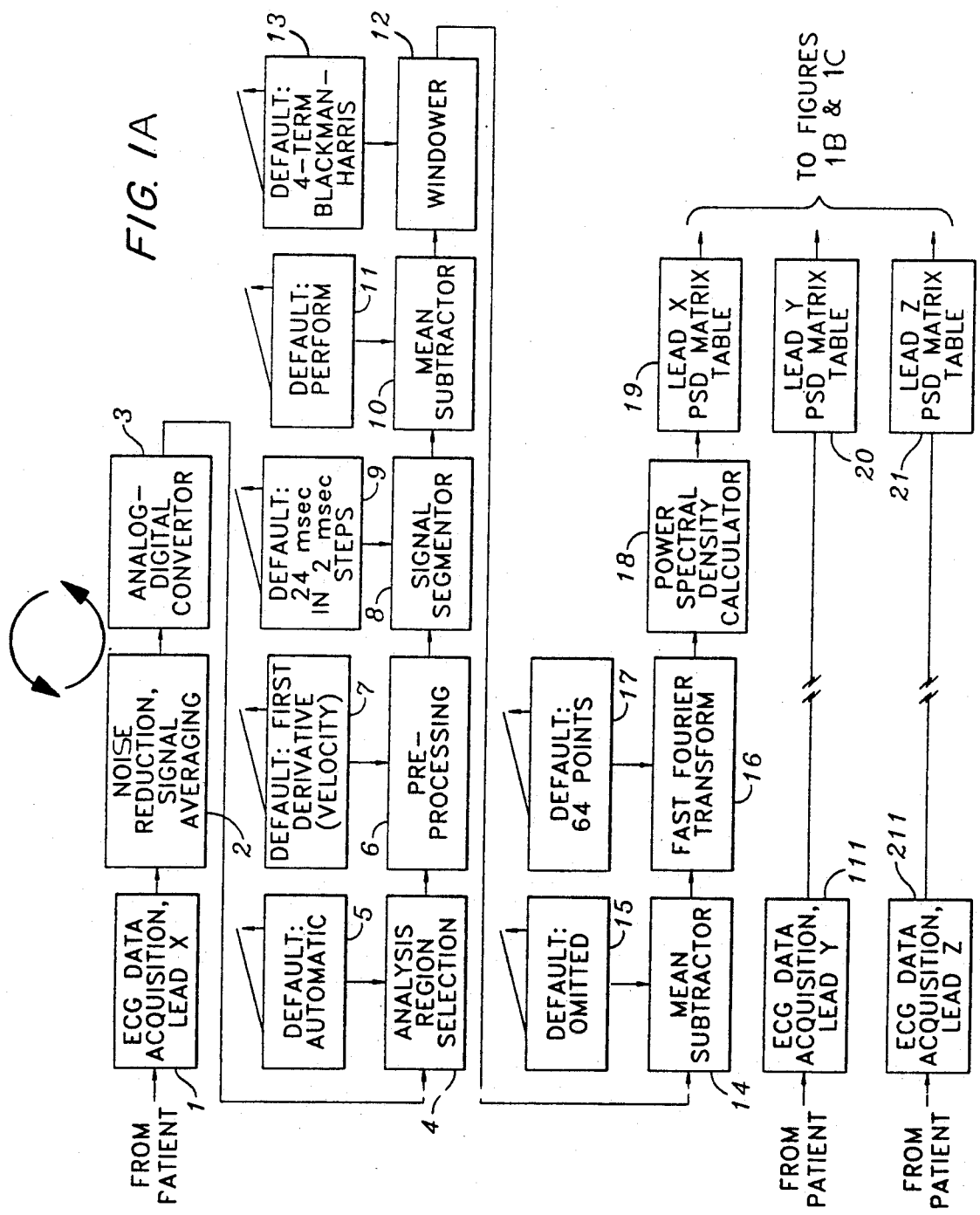
Figure 1B:
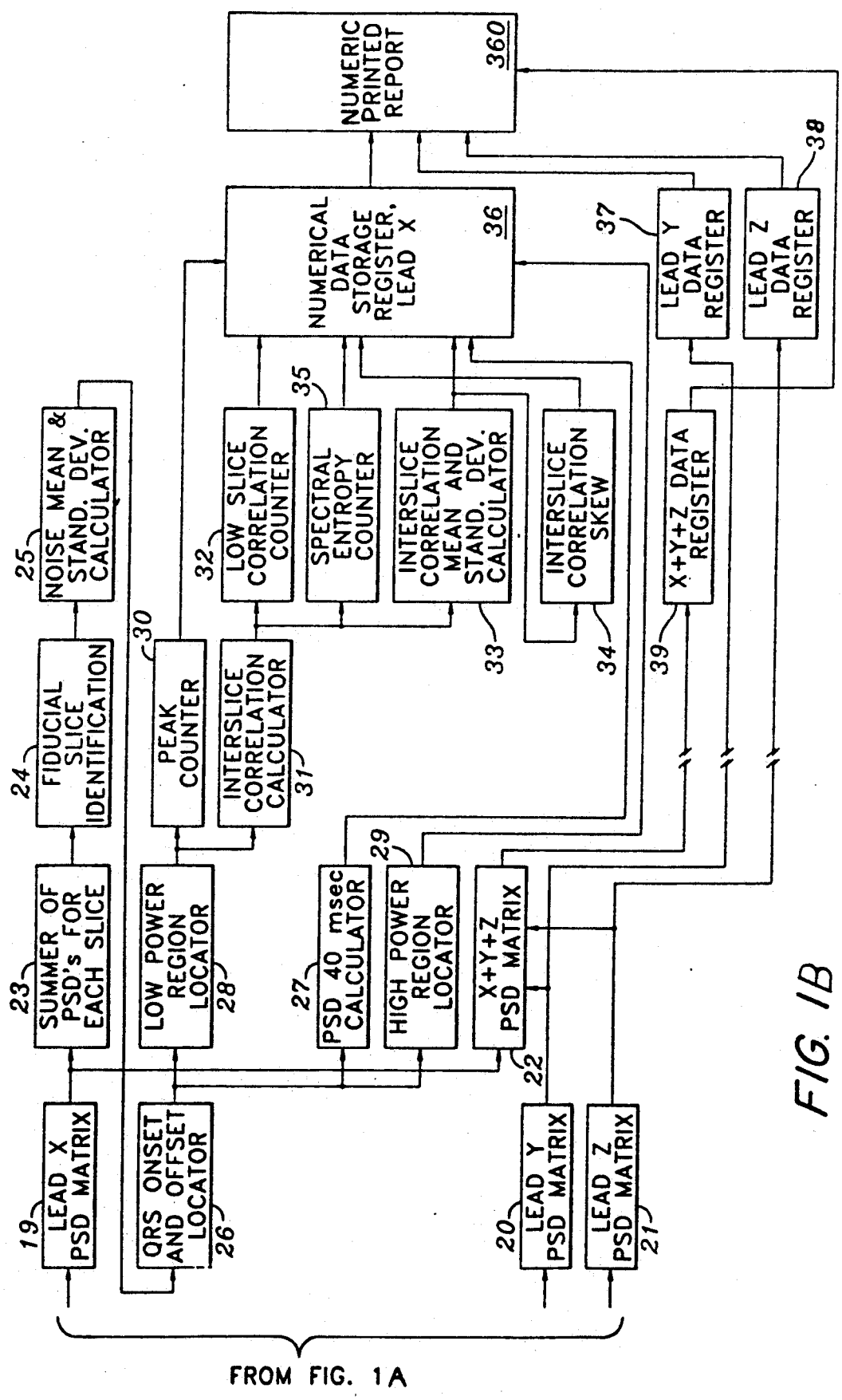
Figure 2A:
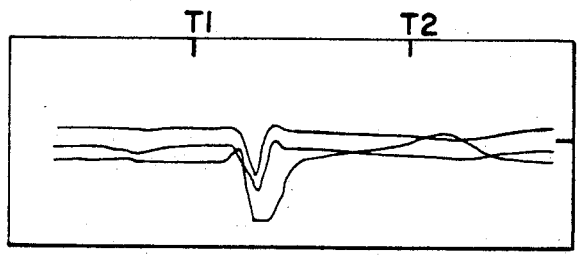
Figure 2B:
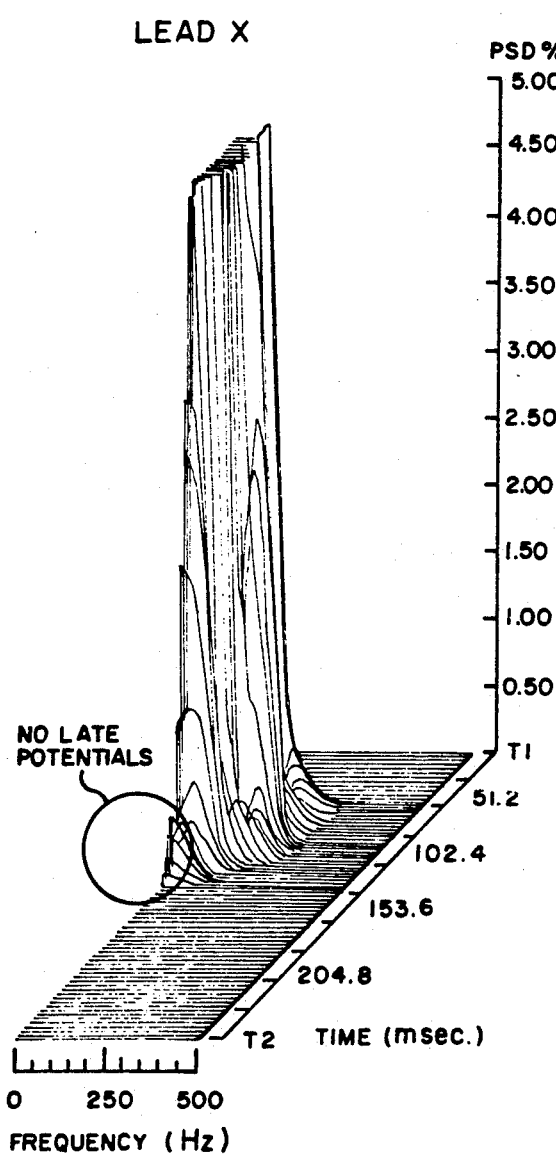
Figure 2C:
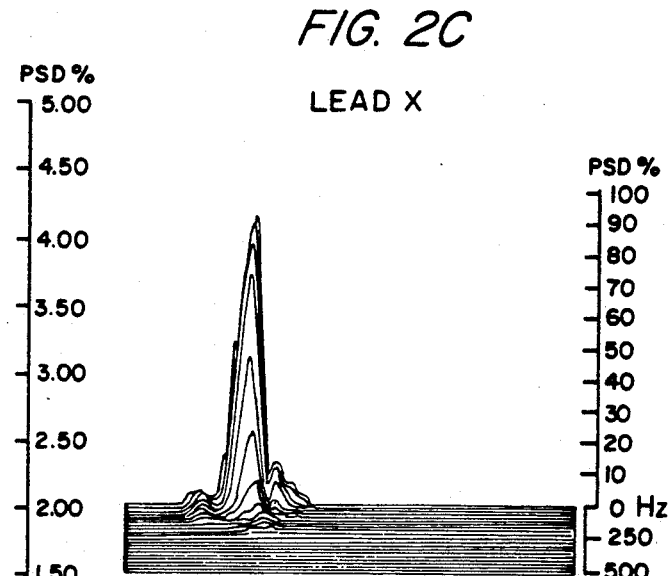
Figure 2D:
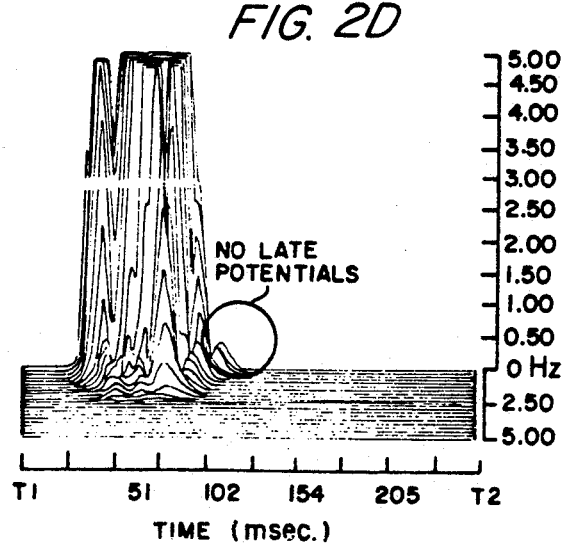
Figure 2E:
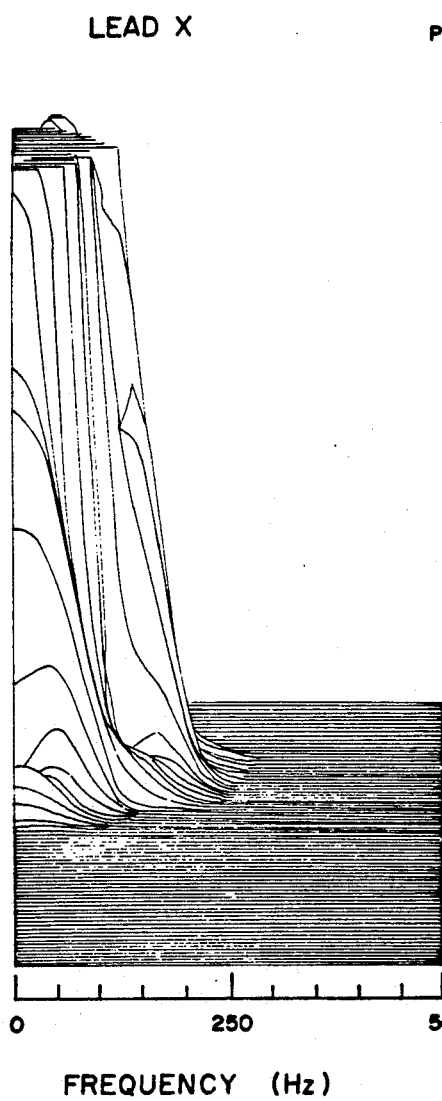
Figure 2F:
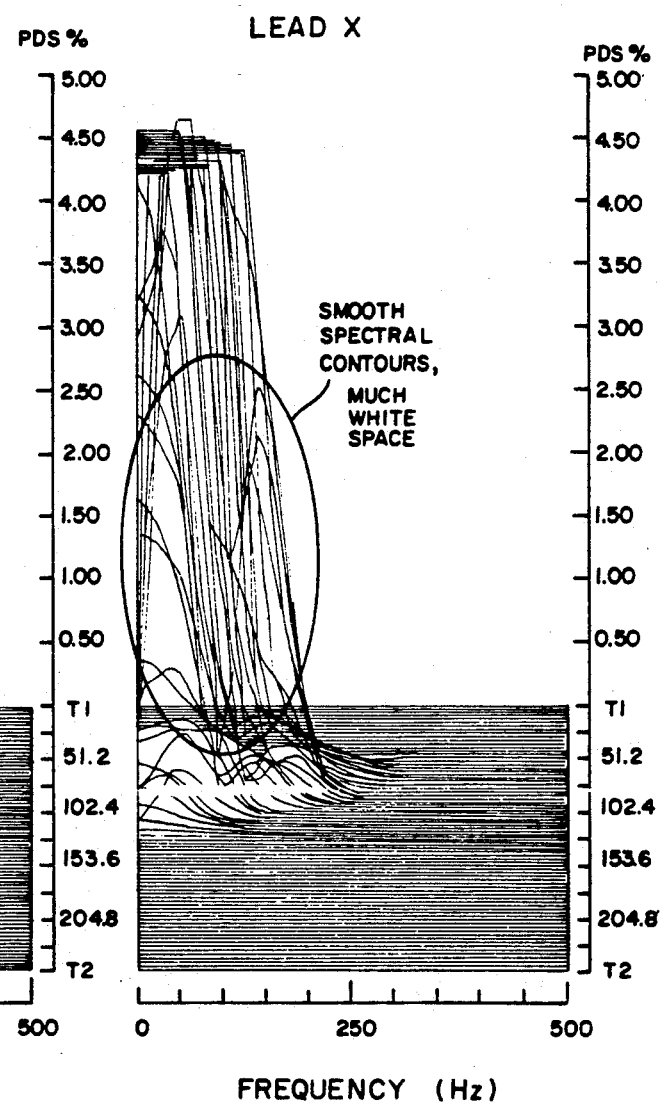

Referring now to FIGS. 1A-1C, a simplified block diagram of the ECG frequency analysis system according to the present invention is shown. As shown in the Figures, most of the processing is performed separately but in identical fashion upon each of three channels (X, Y and Z) of signal averaged surface electrocardiogram. For simplicity, only the processing carried out on channel X is shown in the block diagram, except where there is a combination of data from more than one channel—specifically at blocks 22 and 39.

As shown in FIG. 1A, block 1, three orthogonal channels (X, Y and Z) of bipolar electrocardiographic signal are acquired over a timespan of several hundred beats, either in real time by attachment of an appropriate isolated preamplifier directly to the patient, or from some other source, such as a previously recorded 24-hour Holter tape played back through an appropriate scanning device. At block 2, signal averaging is performed in order to reduce background noise to a level generally considered acceptable for conventional time domain late potential analysis, namely noise less than 1 uV rms from 25-250 Hz. Generally, some 200-500 heart beats need to be averaged to achieve the desired noise reduction. Those skilled in the art will of course recognize that noise reduction and signed averaging could also be done subsequent to conversion of raw data to a digital signal. In this case, the order in FIG. 1 of Noise Reduction and Signal Averaging, block 2, would be interchanged with Analog-Digital Converter, block 3. The actual frequency analysis claimed in this invention commences at block 4, with one, two or three channels of averaged ECG signal, digitized at typically 1000 Hz, with resolution of at least 1.5 uV per bit stored in computer memory or on some permanent storage medium.

In order to accomplish the dual purposes of providing both a standardized routine clinical and a flexible research application facility, analysis can be performed at user option in either of two modes. In automatic (default) mode the whole analysis is carried out upon issue of a single keystroke command, according to a predefined set of processing parameters, culminating in the printing of spectral maps and a numeric printed report. Otherwise, the user may access a menu prior to initiating the analysis, from which alternative analysis parameters in a wide range of permutations and combinations may be selected. Boxes on the figures where such optional user interaction is provided in this invention are identified with a switch symbol, indicating a capability for manual control. User override of the default parameters will henceforth be referred to as "manual" mode in this description.

Returning now to FIG. 1A, at block 4, the region of ECG signal over which the subsequent analysis is to be performed is determined. In default mode, the QRS region is first located by a computer algorithm (many suitable algorithms are known to those versed in the art) and the signal region commencing 25 msec before and terminating 125 msec after the QRS complex is demarcated. In manual mode as shown at block 5, the user indicates by using a mouse operated cursor the onset (beginning) and offset (end) of the region to be analyzed, as well as the orientation to be used for plotting of maps. Because of the three-dimensional nature of the frequency spectral plots as exemplified in FIGS. 2-4, 8 and 9, low amplitude waveforms of interest may be obscured "behind" larger ones. If interest is primarily in signals occurring before the QRS such as the P wave or HIS bundle, then the maps may be plotted with these structures "in front" so as not to be obscured by the much larger QRS waveform itself. On the other hand, if interest is primarily in signals such as late potentials which occur after the QRS (the default condition), then the maps are plotted in reverse direction, with later occurring structures plotted in front of the earlier occurring QRS.

The next step in analysis is signal pre-processing. At block 6 in default mode, the first derivative of the signal is calculated according to the following formula:

$$y[t] = (x[t+1] - x[t-1])/2 + (x[t+2] - x[t-2])/8$$

where y[t] is the new amplitude of the signal at sampling time t, x[t+1] the old amplitude of the next sampled point and so on. In manual mode, the user may elect, as depicted by block 7, to substitute for the processing at block 6 either no signal modification whatever or second derivative calculation according to the formula:

$$y[t] = x[t+1] + x[t-1] - 2(x[t])$$

using the same nomenclature as for the first derivative equation above. Since the undifferentiated ECG signal represents amplitude of the depolarization wavefront as a function of time, the first derivative corresponds to velocity, while the second derivative is analogous to wavefront acceleration. Use of the first derivative in default mode minimizes the undesirable effect whereby a normal but sloping ST segment containing very high energy low frequency signal components obscures the presence of low amplitude late potentials in the spectral plots.

At block 8, the time spanning the signal region of interest is divided into overlapping segments or "time slices" of equal length according to the parameters of block 9. In default mode, slices are of 24-msec duration and each successive slice commences 2 msec later than its immediate predecessor. For example, if the signal region to be analyzed is 240 msec long, then there would be 1+(240-24)/2 slices, or 109 slices submitted to further processing. In manual mode, segment length may range from 5 msec to 150 msec, while step interval may be selected from 1 msec. to 20 msec. Each time slice is then successively processed through blocks 10 to 18 until at block 19 a two dimensional table, FIG. 10, is built in computer memory where each row represents the power spectral densities (PSD) at multiple frequency harmonics of a single time slice while each column contains the PSD's of all time slices at a single frequency, spanning the signal region of interest.

In default mode at block 10, the mean value of the signal is calculated for each time slice and subtracted from each data point within that slice so as to remove any DC offset. As shown in blocks 11 and 15 in manual mode, mean subtraction may be overridden altogether or delayed until after "windowing," i.e., multiplication by a suitable weighing function, performed at block 12.

In default mode at block 12, each time slice is multiplied by a 4-term Blackman-Harris window of equal length, in order to minimize spectral leakage and effects of edge discontinuities inherent in the Fast Fourier Transformation process of block 16. Rectangular, Hanning or Hamming window options may be substituted in manual mode as depicted in block 13.

In manual mode, windowing may be followed by mean subtraction to remove DC offset as shown by blocks 14 and 15, but in the default mode mean subtraction is done prior to windowing.

The next processing step is performance of a discrete Fast Fourier Transform (FFT) on each time slice, at block 16. Preferably, the time slice data values are first moved to the beginning of a memory array which is then padded with zeroes to the length of the desired FFT. In default mode, a 64-point FFT is used but in manual mode 32 to 1024 points may be selected instead (block 17). For a default slice length of 24 msec represented by 25 data points and a 64 point FFT, points 26 to 64 are set to zero after which the double precision FFT is carried out.

At block 18, Power Spectral Densities are next calculated as the sum of the squares of the real and imaginary Fourier coefficients and for each successive time slice placed into the next row of the PSD matrix table at block 19.

The processing of blocks 8 to 18 is repeated for each time slice (and for each ECG lead) to build the PSD matrix tables of blocks 19, 20 and 21 spanning the whole of the signal region of interest. These PSD tables are then used to generate spectral maps as per FIG. 1C or to calculate further numeric parameters as per FIG. 1B.

At FIG. 1B, block 22, a fourth PSD matrix containing the mean values of the X, Y and Z lead matrices is calculated. This "X+Y+Z Average" PSD table is henceforth displayed, plotted and used for numeric quantification in identical fashion to the original X, Y and Z leads.

As will become apparent from later discussion of the visual plots depicted in FIGS. 2-4, 8 and 9, we have discovered that the spectral maps of abnormal subjects are conspicuously "turbulent," with spectral contours less smooth than those of normal persons. The numeric calculations depicted in FIG. 1B, blocks 23 to 35, quantify many of the differences between normal and abnormal maps so as to allow development of precise classification criteria. Each calculated parameter corresponds to a qualitative visual difference apparent from comparison of normal and abnormal spectral maps, as will be discussed below.

It will be recalled that each row of a lead's PSD matrix at block 19 contains the frequency analysis of a single time slice. At FIG. 1B, block 23, an additional column referred to as the "total PSD column" is now added to the table for each ECG lead by summing the PSD at all frequency harmonics for each row to represent the sum total power spectral density at all frequencies for each time slice. At block 24, the fiducial, or reference time slice of the QRS complex is identified as the row with the highest total PSD in the total PSD column just calculated.

Next, at block 25, the mean background noise value and its standard deviation are calculated by identifying the 40 msec region (21 consecutive time slices at the default step interval of 2 msec) within the total PSD column having the lowest average (total) PSD.

At block 26, the time slice rows corresponding to QRS onset and offset are next identified as the furthest rows, moving successively forwards and backwards away from the QRS fiducial slice of block 24, having total PSD at least 5 standard deviations greater than the mean background noise level of box 25.

Also from the total PSD column calculated at block 23, a low power terminal region is defined as commencing at the first time slice following the fiducial QRS slice having total PSD less than 0.2% of the fiducial slice. This region is analogous to the late potential region of conventional time domain analysis. Thus, the total QRS complex demarcated at block 26 is divided at block 29 into a "high power" and at block into a "low power terminal" region.

Meanwhile at block 27, the sum of the total PSD's over the terminal 40 msec of the QRS complex, demarcated at block 26, is calculated. We have discovered that the value of this parameter, known as "PSD40", is higher in normal subjects than in those with time domain late potentials.

A further set of numerical computations is now performed separately upon the low power and high power QRS regions defined at blocks 28 and 29. For brevity, only the low power region calculations are elaborated here, since the processing performed upon the high power main QRS region is identical. One of the conspicuous differences between spectral maps from normal and abnormal subjects is the increased number of spectral peaks evident on the abnormal maps, especially at higher frequencies. Accordingly at block 30, counts are made of spectral peaks within the low power terminal QRS region by six separate criteria. First, peaks are classified according to whether they occur above 250 Hz ("high frequency") or below 250 Hz ("low frequency"). Then, separately for high and low frequencies, counts are made of peaks occurring in the frequency axis along rows of the PSD matrix table ("frequency axis peaks"), in the time axis along columns of the PSD table ("temporal axis peaks") or in both axes simultaneously ("biaxial peaks"). We have found that subjects who have time domain late potentials and ventricular arrhythmias have higher peak counts than subjects with late potentials but no proneness to VT. Significantly, this characteristic of abnormals is true also for peaks counted in the main high power QRS region, as well as in the late potential region.

At block 31, a second additional column is calculated for each lead's PSD matrix table, containing the Pearson correlation coefficient of each row with the row immediately below it. This new column thus represents the degree to which the spectral characteristics of each time slice resemble the spectrum of the adjacent time slice. This column of inter-slice correlation coefficients is later plotted in one of the visual display options at FIG. 1C, block 49, as well as yielding several further numeric criteria of diagnostic importance.

At FIG. 1B, block 32, the number of instances of an inter-slice correlation coefficient having a value less than 0.985 is counted. We have observed that normal subjects have very few instances of poorly correlated time slice pairs, whereas the incidence in patients prone to VT is much higher.

Block 33 depicts calculation of the mean and standard deviation of the correlation coefficients in the column calculated at block 31. The time slices of normal subjects have a higher mean correlation and lower standard deviation than abnormals.

At block 34, the skew of the distribution of correlation coefficients in the column calculated at block 31 is found by dividing the number of instances of correlation coefficient less than the mean value calculated at block 33 by the total number of slices in the low power region. In normal subjects, correlation coefficients are more evenly distributed around their mean than in abnormal subjects.

At block 35, a parameter we call "spectral entropy" is calculated to estimate the degree to which the frequency spectra of time slices differ from the average frequency spectrum of the region. Spectral entropy is calculated as follows. An additional row is added to the PSD matrix table to contain the calculated average PSD at each harmonic frequency of the rows representing the time slices of the low power region. The average correlation of each time slice row with this new row of average PSDs is next calculated and then subtracted from 1 to yield the spectral entropy statistic for the region. We have found that normal subjects have lower spectral entropy values than abnormals.

Figure 5:
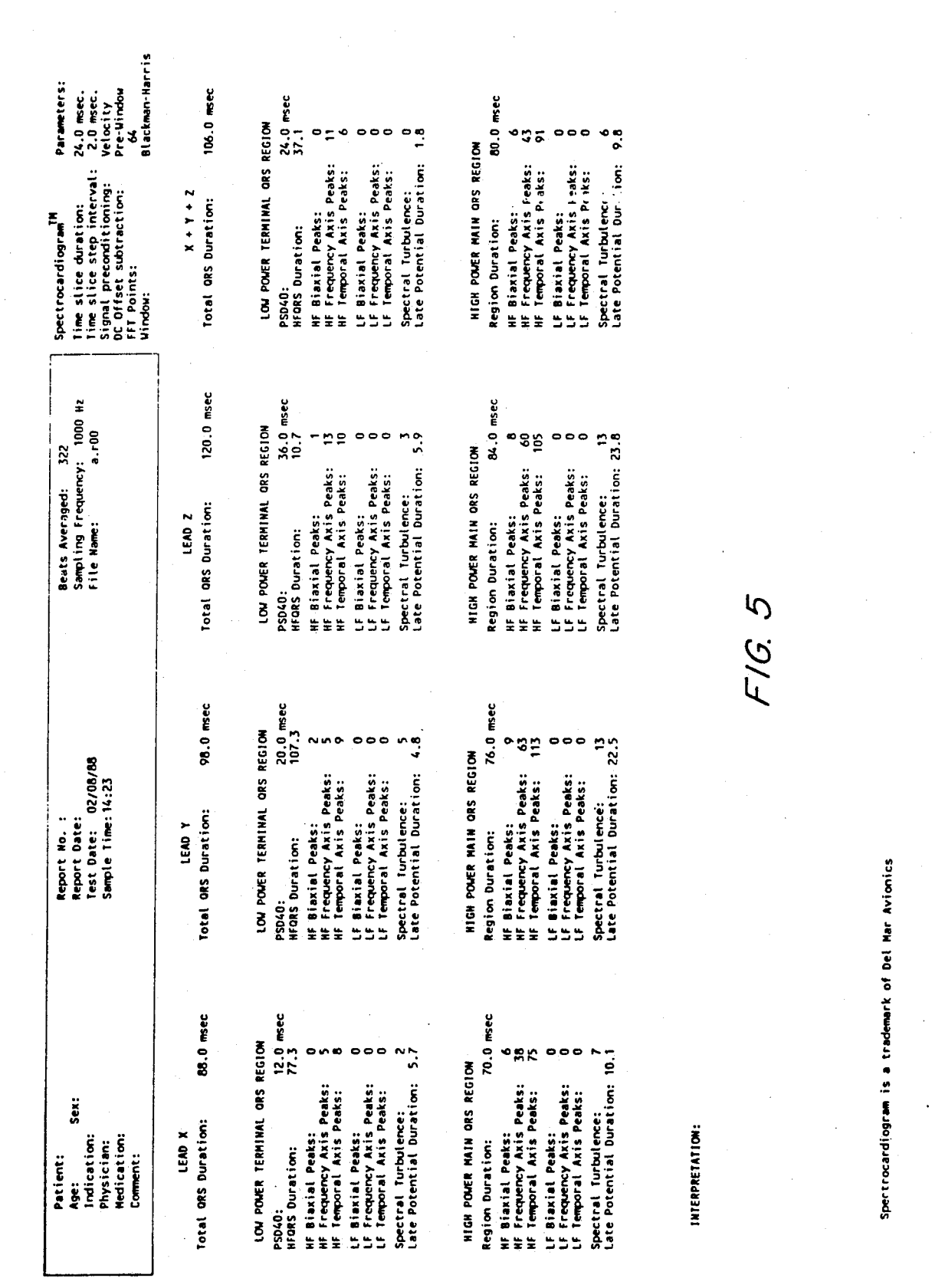

At block 36, the numeric parameters derived at blocks 27 to 35 are collected together to form the numeric parameters for lead X, which at block 360 is combined with identically derived numerics from leads Y, Z and the synthesized XYZ average matrix to make up the printed numeric report exemplified in FIGS. 5 through 7.

Returning now to blocks 19, 20, 21 and 22 representing the PSD matrix tables, FIG. 1C illustrates how these tables are used to generate visual CRT displays and the printed spectral maps exemplified in FIGS. 2-4, 8 and 9.

At FIG. 1C, block 41 in manual mode, the user may optionally elect to display or plot not the values actually contained in the PSD matrix tables but rather their first or second derivatives with respect to time. In default mode, no calculations or changes are made at block 40. If first derivative ("velocity") post-processing is selected at block 41, each time slice row is subtracted from the row above it thus representing the change in PSD at each slice step. If second derivative post-processing ("acceleration") is selected, then each time slice row is subtracted from the mean of the row immediately above and the row immediately below it. These optional post-processing steps accentuate some of the visual differences between the maps of normals and abnormals.

At block 42, the display and plotting gain is determined. The gain used in default mode is 20, such that full scale corresponds to 5% peak PSD, a value found by experimentation to yield good resolution of the visual features useful in clinical diagnosis. In manual mode the user may, at block 43, select gains from 0.01 to 1000.

At block 44, the orientation of spectral maps to be drawn and/or displayed is determined. Inspection of FIGS. 2-4, 8 and 9 will disclose the utility of being able to view these three dimensional structures from multiple angles, since no single view is ideal for looking at all features of potential interest. In default mode, all available views are automatically printed, but this may be overridden in manual mode at block 45 to select single or restricted combinations of views.

In addition to gain and view selection, the invention provides for optional non-linear scale compression in manual mode prior to display or plotting. In default mode, PSD values are used but as depicted at block 47. In manual mode the user may select Power (square root of PSD) or logarithmic (dB) representation of the spectral data instead.

EXAMPLES OF OPERATION

Figure 3A:
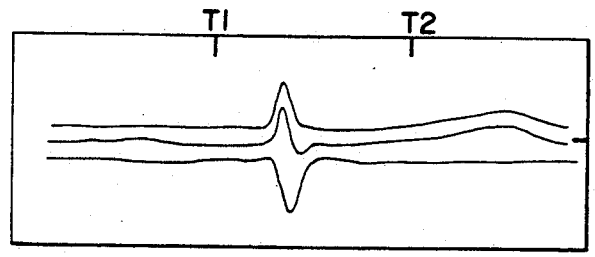
Figure 3B:
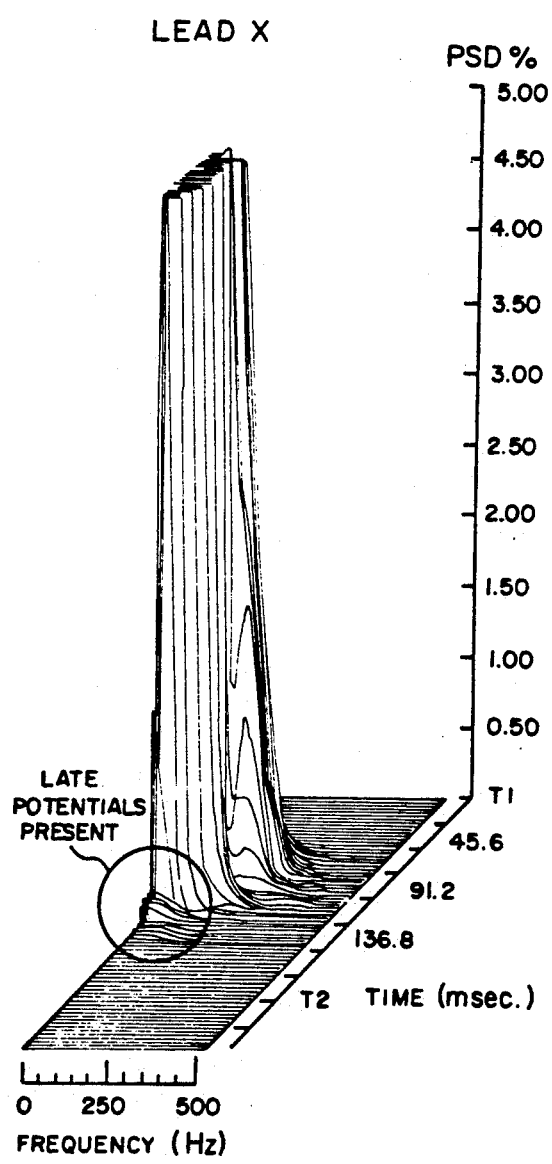
Figure 3C:
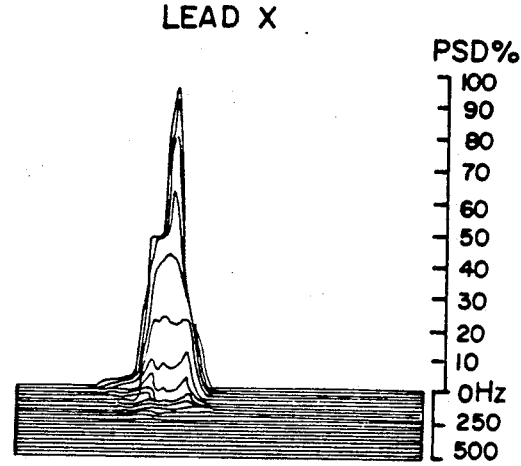
Figure 3D:
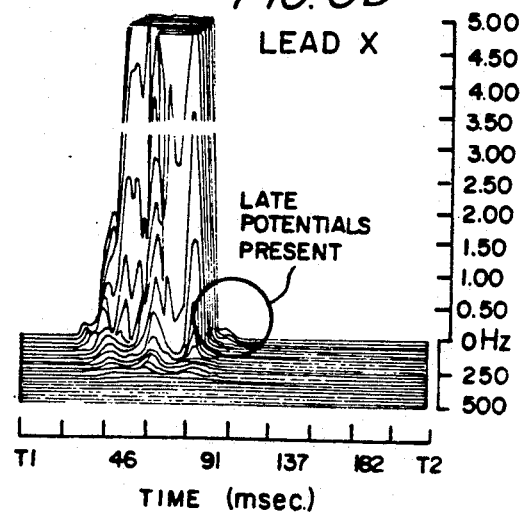
Figure 4A:
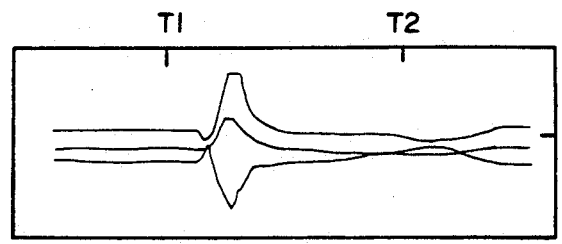

Referring now to FIGS. 2A-2F through 4A-4F, some specific examples of the benefits of the invention are shown by recordings made from actual patients FIGS. 2A-2F and 3A are both from normal healthy volunteers with no heart disease and no proneness to ventricular arrhythmia. FIGS. 4A-4F is from a patient who has suffered a heart attack and has had multiple episodes of life threatening arrhythmia. Although not at risk, the subject of FIGS. 3A-3F has a common minor normal variant of the electrocardiogram known as "Incomplete Right Bundle Branch Block" which results in the end portion of the QRS complex being slightly slurred. Such slurring results in a "false positive" late potential, and the subject of FIGS. 3A-3F would be classified as "at risk" on the basis of a test for presence of late potentials. The late potential signals are indicated as the circled regions on FIGS. 3A-3F and 4A-4F. As shown by the circled regions of FIGS. 3A-3F and 4A-4F, the spectrocardiograms of both patients have low amplitude undulations which extend beyond the end of the higher amplitude main QRS region. For orientation purposes, the standard ECG signal is shown in FIGS. 3A and 4A, with labels T1 and T2 indicating the positions in time corresponding to the limits of spectral plots 3B-3F and 4B-4F. On each of the spectral plots 3B-3F and 4B-4F, times T1 and T2 are marked to indicate on a time axis the beginning and end of a time interval in which an ECG signal is analyzed to produce the corresponding spectrocardiograms. Thus, in FIGS. 3D and 4D, time progresses from left to right, while in FIGS. 3B and 4B, time progresses obliquely from upper right to lower left. Therefore, late potentials appear to the right of the main high amplitude QRS region in FIGS. 3D and 4D, and to the lower left of that high amplitude region in FIGS. 3B and 4B.

Figure 4B:
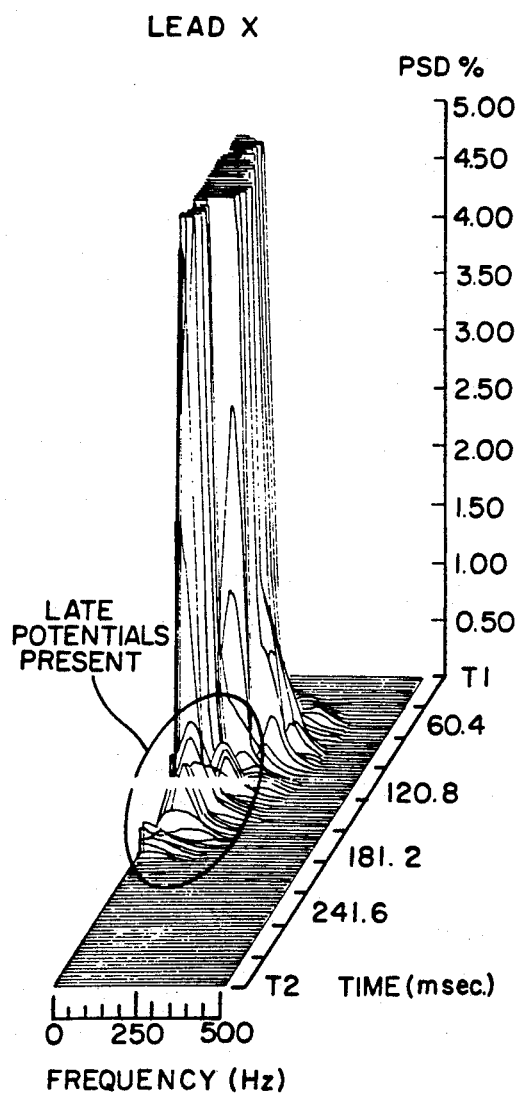
Figure 4C:
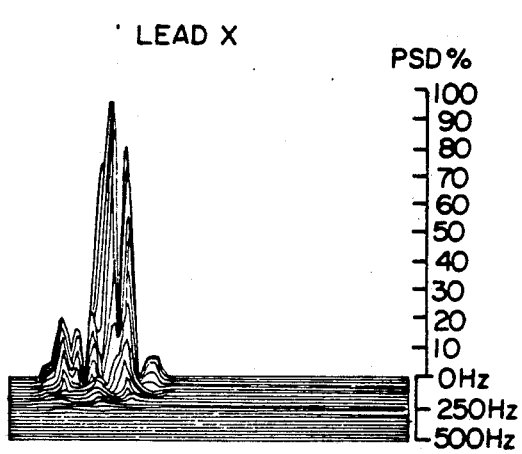
Figure 4D:
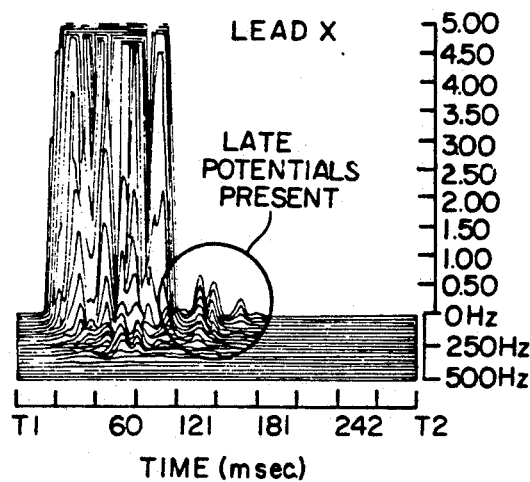
Figure 8A:
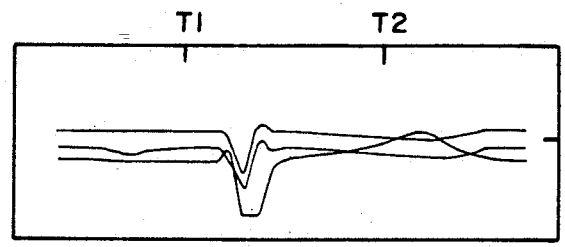
Figure 8B:
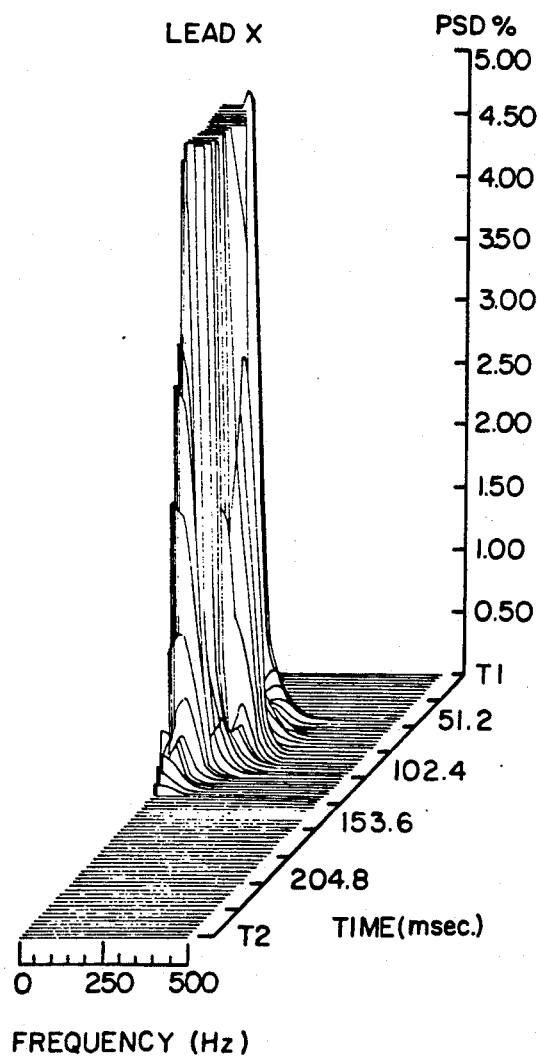
Figure 8C:
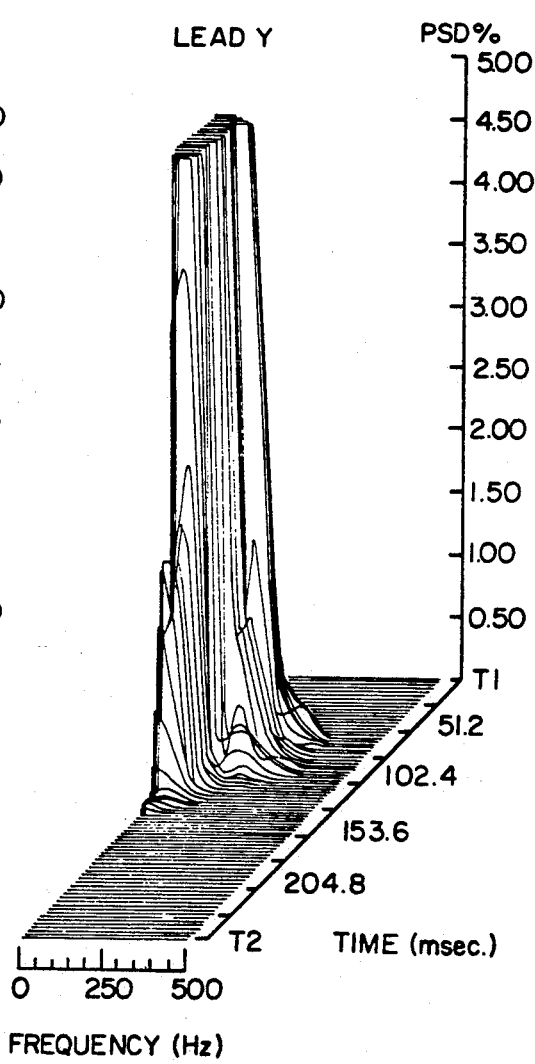
Figure 8D:
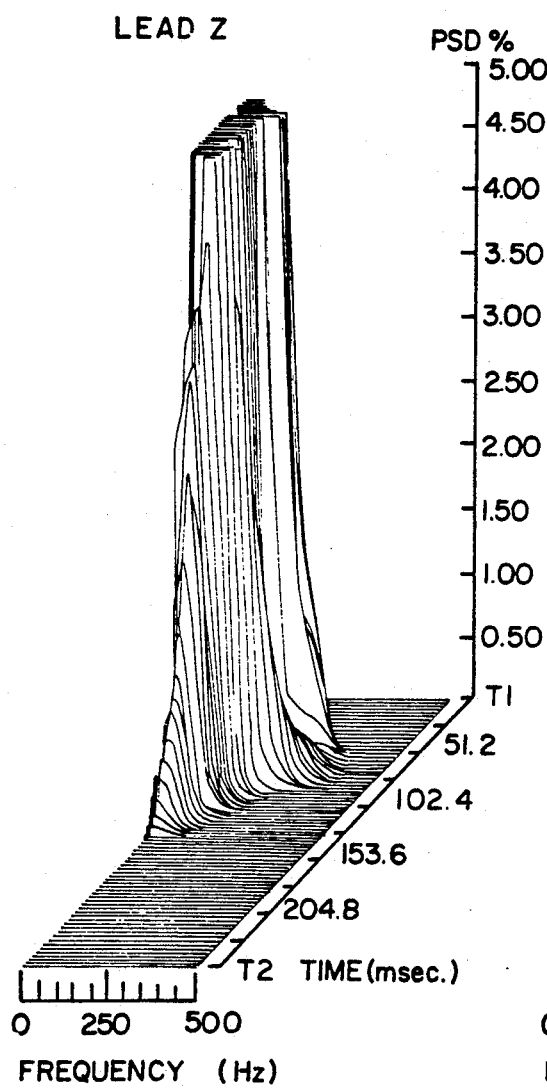
Figure 8E:
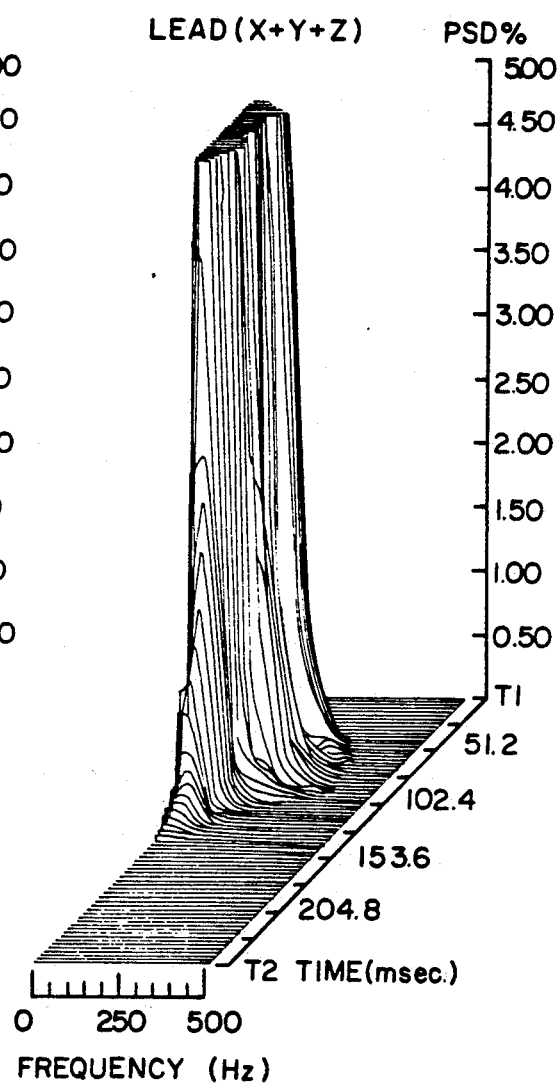
Figure 9A:
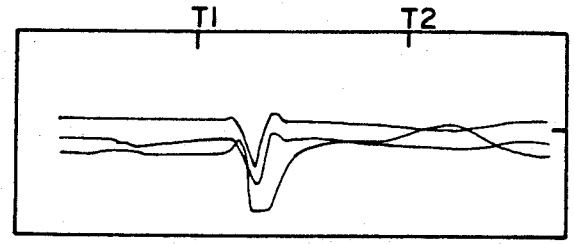
Figure 9B:
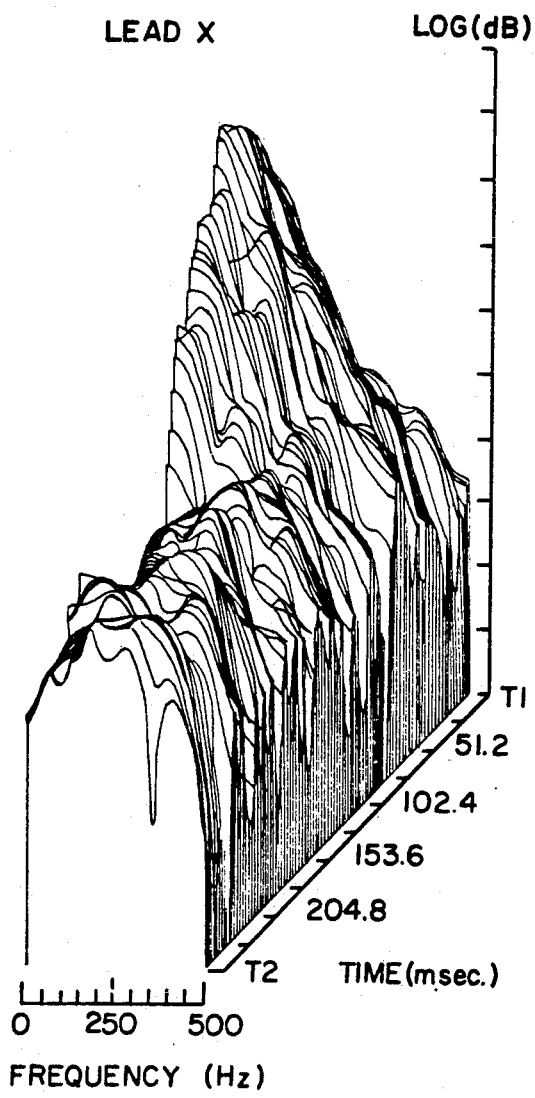
Figure 9C:
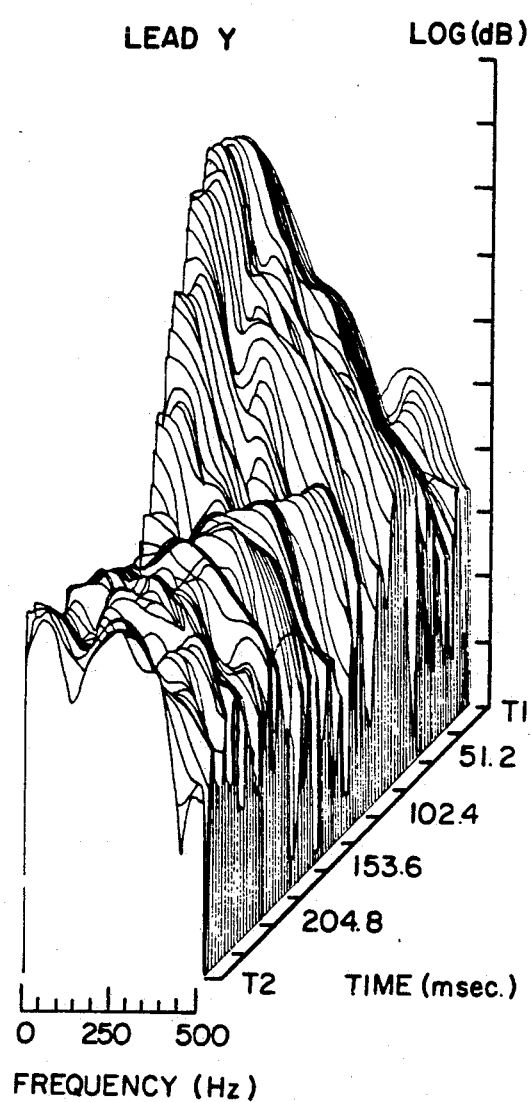
Figure 9D:
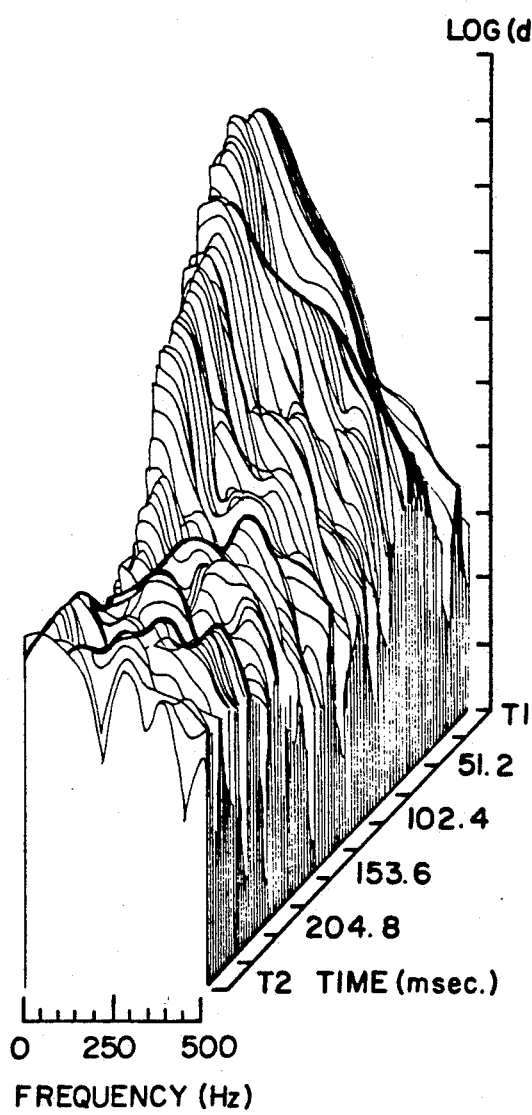
Figure 9E:
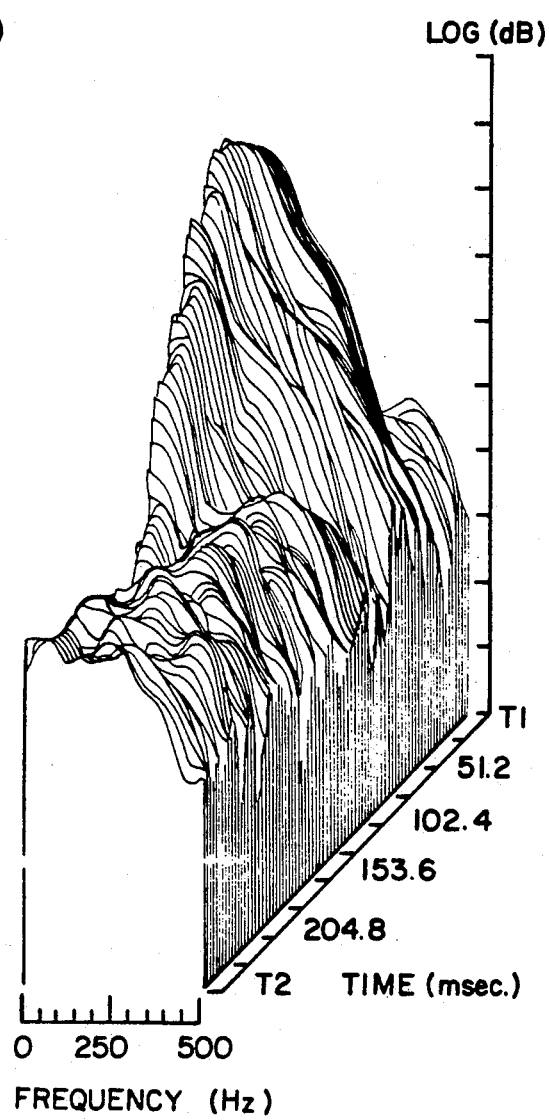

As shown by the circled regions of FIGS. 4B, 4D and 4F, from the patient with serious arrhythmias, the undulations have many sharp peaks and frequent changes in shape from one time slice to another. In contrast, the corresponding circled regions of FIGS. 3B, 3D and 3D, from the "false positive" patient, display contours which are much less turbulent, with relatively smooth transitions from one time slice to an adjacent time slice. To use a topographical analogy, the late potential "terrain" is very much "rougher" in the spectrocardiograms of the true positive subject than in those of the false positive subject. This difference in the smoothness of spectral contours is also evident within the high amplitude QRS region proper, as best seen in FIGS. 4D and 4F where the greater "roughness" of the terrain results in much less white space within the whole QRS region than in corresponding FIGS. 3D and 3F from the false positive subject. Note how both patients have low amplitude signals extending out beyond the end of the QRS complex. However, in FIG. 3 ("false positive"), the spectral contours of the late potentials are smooth, whereas in FIGS. 4A-4F ("true positive") the spectral contours are turbulent and disorganized. Note also how much more turbulent the spectral contours appear throughout the whole QRS complex (not just the late potential region) in the "true positive" patient of FIG. 4.

The above examples illustrate one instance of how the present invention provides a means for determining the correct risk classification of a patient who would be misdiagnosed as "at risk" by techniques of the prior art.

FIG. 5 is the numeric report of a healthy volunteer generated from the spectral plot shown in FIG. 2.

FIG. 6 is the numeric report generated from the "false positive" patient whose spectral plots are shown in FIGS. 3A-3F, while FIG. 7 is from the "true positive" patient of FIGS. 4A-4F. Comparing the numerical data of FIG. 6 from the "false positive" healthy volunteer with corresponding data of FIG. 7 from the "true positive" patient, it may be seen that there are conspicuous differences in many of the parameters listed. For example, HF (high frequency) peak counts and spectral turbulence values in FIG. 6 are almost double those in FIG. 7. Exact cutoff or demarcation points between numerical values for normal and at-risk patients will have to be determined by clinical experiments. The differences visually observed in the spectral plots result in correspondingly different calculated numeric data, enabling specific numeric criteria of abnormality to be developed for diagnostic purposes.

FIGS. 8A-8E and 9A-9E are spectral plots generated by the apparatus of FIG. 1, from the same raw data from the healthy volunteer used to generate FIGS. 2 and 5. However, in FIGS. 8A-8E and 9A-9E, the default analysis protocol of the apparatus has been modified by operator intervention, as follows.

FIGS. 8A-8E displays on a linear vertical, or ordinate the amplitude of power spectral densities of the ECG waveform from three orthogonal lead sets, X, Y, and Z, plus a fourth spectrocardiogram of the sum of the signals from the X, Y and Z leads.

FIGS. 9A-9E shows the power spectral densities for the same lead configuration as FIGS. 8A-8E, but with the power spectral densities displayed on a logarithmic (db) scale, rather than a linear scale.

It should be recognized that FIGS. 8A-8E and 9A-9E are just two examples from a very large number of variations in display format which are made possible by the novel method and apparatus of the present invention. Some of these variations may prove useful in the detection of other anomalies in ECG's or other bioelectrical signals, in addition to the displays of FIGS. 3A-3F and 4A-4F which clearly demonstrate the power of the present invention to distinguish between false positives and patients who are truly at risk.

What is claimed is:

1. A method for detecting abnormalities in physiological functions of an organism by performing a frequency analysis of a single cycle of a time varying bioelectric signal, said method comprising:
    (a) partitioning said single cycle of said time varying signal into a sequence of time-displaced, overlapping segments or slices,
    (b) performing a frequency analysis of each of said slices, thereby resolving each of said slices into a sequence of discrete spectral components of varying amplitude,
    (c) storing a number proportional to the magnitude of each of said spectral components in a table in which frequency is plotted along a first axis, and time is plotted along a second axis,
    (d) assessing the degree of difference between the spectra of different slices of said table, and (e) comparing said spectral differences with corresponding differences obtained from representative samples of normal and abnormal test organisms.

2. The method of claim 1 in which said frequency analysis is further defined as a Fourier analysis.

3. The method of claim 2 wherein said Fourier analysis is further defined as a discrete fast Fourier transform (FFT).

4. The method of claim 3 wherein said discrete FFT is performed on overlapping segments of a selected portion of said signal.

5. The method of claim 4 further including the step of signal averaging said bioelectric signal prior to performing said FFT.

6. The method of claim 5 further including multiplying the amplitude of said signal by a windowing function prior to performing said FFT, thereby minimizing spectral leakage and effects of edge discontinuities inherent in said FFT process.

7. The method of claim 6 further including the step of displaying said spectral components on a contour plot approximating a three-dimensional plot in which frequency is plotted along one axis, the amplitude of each spectral component is plotted along a second axis, and time is plotted along a third axis, thereby facilitating a visual assessment of the degree of irregularity or spectral turbulence in said signal which may be associated with a physiological defect.

8. The method of claim 6 further including displaying numbers calculated from values of said spectral components.

9. The method of claim 4 further including the steps of calculating the mean value of the amplitude of each of said slices and subtracting said mean value from the instantaneous value of each said slice prior to performing said FFT.

10. A method for analyzing in the frequency domain a single cycle of an ECG signal, which single cycle may be an ensemble average of a plurality of cycles, said method comprising:

a. locating within said ECG signal, a time interval of interest, typically the QRS region of said ECG signal;
b. dividing said time interval of interest into a sequence of overlapping segments, or slices;
c. multiplying each said slice by a windowing function to form a windowed slice;
d. performing a discrete fast Fourier transform (FFT) on each said windowed slice, in which FFT the power spectral density (PSD) at a sequence of frequencies is calculated;
e. producing a numerical matrix or table of PSD's in which discrete frequencies head each column in said table and discrete times head each row of said table, thereby resulting in a matrix of PSDs for a vertically-stacked array of time-slices, and,
f. comparing said matrix of PSD s with corresponding matrices obtained from representative samples of normal and abnormal test subjects.

11. The method of claim 10 further including calculating the mean value of the amplitude of each time slice prior to performing said FFT.

12. The method of claim 11 further including subtracting said mean value of each time slice from each data point within that time slice, thereby removing any D.C. offset in said time slice.

13. The method of claim 10 further including performing steps (a) through (f) on at least one additional ECG signal obtained from a patient simultaneously with said first ECG signal, thereby obtaining a plurality, N, of ECG signals and N PSD matrices.

14. The method of claim 13 further including calculating the mean values of each time slice of each ECG signal of said plurality of signals.

15. The method of claim 14 further including subtracting said mean value of each time slice of each of said ECG signals from each data point within that time slice, thereby removing any D.C. offset in said time slice.

16. The method of claim 14 further including summing said mean values of said N PSD matrices, thereby forming a (N+1)th average PSD matrix.

17. The method of claim 10 further including summing each PSD value in a time slice row to form a total PSD sum, thereby forming a total PSD column.

18. The method of claim 17 further including comparing each total PSD value in each vertical position in said PSD column with each other PSD value to determine that time slice row having the highest total PSD value, and designating said time slice row as the fiducial, or reference time slice of said QRS complex.

19. The method of claim 18 further including locating the onset and offset of the QRS portion of said ECG signal.

20. The method of claim 19 wherein said method of locating said onset and offset of said QRS portion of said ECG signal comprises:
(a) calculating the mean background noise value and standard deviation of said ECG signal represented by said total PSD matrix by identifying a given time interval, represented by a pre-determined number of consecutive time slices within said PSD matrix having the lowest average total PSD; and
(b) identifying that uppermost (earliest) row and lowermost (latest) row away from said QRS fiducial slice having a total PSD at least N1 standard deviations greater than said mean background noise.

21. The method of claim 20 further including calculating the sum of the total PSD's over a terminal interval T1 of said QRS complex.

22. The method of claim 20 further including dividing said QRS region of said PSD matrix into a low power terminal region, and a high power region, said low power terminal region being defined as commencing at the first time slice following said fiducial QRS slice having a total PSD less than a percentage P1 of said fiducial slice, and ending at the termination of the QRS complex, and said high power region of said QRS region being defined as the remainder of said QRS region of said PSD matrix.

23. The method of claim 22 further including separate processing of said low power region data and said high power region data.

24. The method of claim 23 further including counting those peaks or maxima occurring along the frequency axis or rows of said PSD matrix table (frequency axis peaks) below a predetermined frequency F1 and storing for display the number LFP corresponding to said count, and counting those peaks or maxima occurring above said frequency F1 and storing for display the number HFP corresponding to said second count.

25. The method of claim 23 further including counting those peaks or maxima occurring along said time axis or columns (temporal axis peaks) and storing for display a number TP corresponding to said count.

26. The method of claim 25 further including subdividing for display said number TP into a low frequency count LTP for temporal axis peaks below a frequency F2 and a high frequency count HTP for temporal axis peaks above said frequency F2.

27. The method of claim 26 further including counting those peaks or maxima occurring simultaneously along the frequency axis or rows of said PSD matrix and along said time axis or columns of said PSD matrix, and storing for display a number TBP (total biaxial peaks) corresponding to said count.

28. The method of claim 27 further subdividing for display said number TBP into a low frequency count LBP for biaxial peaks below a frequency F3 and a high frequency count HBP for biaxial peaks above said frequency F3.

29. The method of claim 23 further including calculating for each lead's PSD matrix table the Pearson correlation coefficient of each row with the row immediately below it (inter-slice correlation coefficient) and storing for display an additional column of numbers corresponding to said correlation coefficients.

30. The method of claim 29 further including counting the number LISC of said inter-slice correlation coefficients below a pre-determined number N2, and storing for display said number.

31. The method of claim 29 further including calculating and storing for display the mean of said inter-slice correlation coefficients (MISC) and standard deviation of said inter-slice correlation coefficients (SDIC).

32. The method of claim 31 further including calculating and storing for display a number SKISC corresponding to the skew of the distribution of said inter-slice correlation coefficients by dividing the number of instances of said inter-slice correlation coefficient being less than said mean value MISC, by the total number of said slices.

33. The method of claim 29 further including calculating and storing for display a number called spectral entropy by adding an additional row to said PSD matrix table, said additional row containing the calculated average PSD at each harmonic frequency of selected rows of said PSD, calculating the average correlation of each time slice row with the new row of average PSDs, and subtracting said average correlation from 1.

34. An apparatus for analyzing ECG signals to detect abnormalities of electrical conduction within the heart comprising:
   (a) means for selectably storing a waveform representative of the amplitude-versus-time variation of a single cycle of said ECG signal, or an ensemble average of said cycles;
   (b) means for locating within said waveform a time interval of interest;
   (c) means for dividing said time interval into a sequence of overlapping segments, or time slices;
   (d) means for performing a frequency analysis of each of said overlapping segments;
   (e) means for producing a numerical matrix table of the amplitude of each frequency component obtained by said frequency analysis means, said matrix table having in a first line of headings discrete frequency values, and in a second orthogonal line of headings, discrete time intervals corresponding to the beginning of each slice, and
   (f) means for comparing said table with corresponding tables obtained from normal and abnormal test subjects.

35. The apparatus of claim 34 wherein said means for performing said frequency analysis is further defined as effective in determining the relative amplitude of discrete Fourier components, or power spectral density components (PSD's), into which said waveform may be resolved.

36. The apparatus of claim 35 further including means for calculating the mean value of the time-domain amplitude of each of said time slices, prior to performing said frequency analysis.

37. The apparatus of claim 36 further including means for subtracting said mean time-domain value of each time slice from each data point value within that slice, thereby removing any D.C. offset in said time slice.

38. The apparatus of claim 36 further including means for summing each PSD value in a time slice row to form a total PSD sum, thereby forming a total PSD column.

39. The apparatus of claim 38 further including means for comparing the total PSD value in each vertical position in said PSD column with each other PSD value and determining that time slice row having the highest total PSD value, thereby determining a fiducial or reference time slice of the QRS complex of said ECG waveform.

40. The apparatus of claim 39 further including means for locating the onset and offset of said QRS portion of said ECG signal.

41. The apparatus of claim 40 further including means for calculating the sum of the total PSD's over a terminal interval T1 of said QRS complex.

42. The apparatus of claim 41 further including means for segmenting said QRS region of said PSD matrix into a low power terminal region and a high power region, said low power terminal region being defined as commencing at the first time slice following said QRS slice having a total PSD less than a percentage P1 of said fiducial slice, and ending at the end of said matrix, and said high power portion of said QRS region being defined as the remainder of said QRS portion of said PSD matrix.

43. The apparatus of claim 42 wherein said further including means for further separate processing of said low power terminal region and said high power region, said means for further processing (as defined as) including means for counting those peaks or maxima occurring along the frequency axis rows of said PSD matrix table (frequency axis peaks), those peaks or maxima occurring along the time axis or columns of said PSD matrix table (temporal axis peaks), and those peaks occurring in both axis simultaneously (biaxial peaks).

44. The apparatus of claim 43 further including means for calculating for each said PSD matrix table the Pearson correlation coefficient of each row with the row immediately below it (inter-slice correlation coefficient) and storing for display an additional column of numbers corresponding to said correlation coefficients.

45. The apparatus of claim 44 further including means for counting the number LISC of said inter-slice correlation coefficients below a pre-determined number N2, and storing for display said number.

46. The apparatus of claim 45 further including means for calculating and storing for display the mean of said inter-slice correlation coefficients (MISC) and the standard deviation of said inter-slice correlation coefficients (SDIC).

47. The apparatus of claim 46 further including means for calculating and storing for display a number SKISC corresponding to the skew of the distribution of said inter-slice correlation coefficients by dividing the number of instances of said inter-slice correlation coefficients being less than said mean value, by the total number of said slices.

48. The apparatus of claim 44 further including means for calculating and storing for display a number called spectral entropy by adding an additional row to said PSD matrix table, said additional row containing the calculated average PSD of each harmonic frequency of selected rows of said PSD, calculating the average correlation of each time slice row with the new row of average PSD's, and subtracting said average correlation from 1.

49. The apparatus of claim 35 wherein said means (a) through (e) are further defined as being capable of performing their indicated functions on a plurality of separate ECG channels.

50. The apparatus of claim 35 wherein said means (a) through (e) are further defined as being capable of performing their indicated functions on a plurality of ECG channels comprising at least a first, X, channel, a second Y, channel, and a third, Z, channel.

51. The apparatus of claim 50 further including means for calculating the mean value of the time-domain amplitude of each time slice to each of said plurality of ECG channels, prior to performing said frequency analysis.

52. The apparatus of claim 51 further including means for subtracting said mean time-domain value of each time slice from each data point value within that slice, thereby removing any D.C. offset in said time slice.

53. The apparatus of claim 52 further including means for summing the mean PSD values of each time slice row of each of said PSD matrices to form a fourth, average PSD matrix table.

54. The apparatus of claim 34 further including means for displaying tables of numbers derived from numbers in said matrix tables.

55. The apparatus of claim 54 further including means for displaying in three-dimensional-like contour plots the amplitude of said spectral components versus time and frequency.

56. The apparatus of claim 55 further including controller means for controlling in an automatic sequence the operation of each of said other means of said apparatus means in performing a frequency domain analysis of said ECG signals according to predetermined default parameters, said controller means being so structured as to facilitate manual change of the values of said parameters by an operator for performing a specific analysis for a specific purpose.

57. The apparatus of claim 56 wherein said selected parameters include:
(a) region of interest;
(b) pre-processing function;
(c) slice duration;
(d) sub-slice (step) duration;
(e) performing of mean subtraction;
(f) type of window function;
(g) number of FFT points; and
(h) orientation and magnification of threedimensional contour maps.

58. The apparatus of claim 55 wherein said means for displaying said spectral components includes visually discernible determination means to provide for correct patient risk classification.

59. The apparatus of claim 58 wherein said visually discernible determination means consists of:
visually discernible means for determining false positive patients wherein said spectral components, displayed by said means for displaying have smooth contours, and
visually discernible means for determining true positive patients wherein said spectral components, displayed by said means for displaying, have turbulent and disorganized contours.

* * * * *

UNITED STATES PATENT AND TRADEMARK OFFICE
CERTIFICATE OF CORRECTION

PATENT NO. : 5,109,862
DATED : May 5, 1992
INVENTOR(S) : Kelen et al

It is certified that error appears in the above-indentified patent and that said Letters Patent is hereby corrected as shown below:

The drawing sheet, consisting of Figs. 5 and 7, should be deleted to be replaced with the sheet of drawings, consisting of Figs. 5 and 7, as shown on the attached page.

Signed and Sealed this

Twenty-sixth Day of October, 1993

Attest:

BRUCE LEHMAN

Attesting Officer

Commissioner of Patents and Trademarks

| PATIENT: | SEX: | REPORT NO.: | BEATS AVERAGED: 322 | SPECTROCARDIOGRAM™ PARAMETERS: |
|---|---|---|---|---|
| AGE: | | REPORT DATE: | SAMPLING FREQUENCY: 1000 Hz | TIME SLICE DURATION: 24.0 MSEC |
| INDICATION: | | TEST DATE: 02/08/88 | FILE NAME: A.R00 | TIME SLICE STEP INTERVAL: 2.0 MSEC |
| PHYSICIAN: | | SAMPLE TIME: 14:23 | | SIGNAL PRECONDITIONING: VELOCITY |
| MEDICATION: | | | | DC OFFSET SUBTRACTION: PRE-WINDOW |
| COMMENT: | | | | FFT POINTS: 64 |
| | | | | WINDOW: BLACKMAN-HARRIS |

| LEAD X | LEAD Y | LEAD Z | X + Y + Z |
|---|---|---|---|
| TOTAL QRS DURATION: (MSEC) 69.0 | TOTAL QRS DURATION: (MSEC) 98.0 | TOTAL QRS DURATION: (MSEC) 120.0 | TOTAL QRS DURATION: (MSEC) 106.0 |

LOW POWER TERMINAL QRS REGION

| | LEAD X | LEAD Y | LEAD Z | X+Y+Z |
|---|---|---|---|---|
| PSD40: | | | | |
| HFQRS DURATION: (MSEC) | 12.0 | 20.0 | 36.0 | 24.0 |
| | 77.3 | 107.3 | 10.7 | 37.1 |
| HF BIAXIAL PEAKS: | 2 | 2 | 1 | 0 |
| HF FREQUENCY AXIS PEAKS: | 5 | 5 | 13 | 11 |
| HF TEMPORAL AXIS PEAKS: | 8 | 9 | 10 | 6 |
| LF BIAXIAL PEAKS: | 0 | 0 | 0 | 0 |
| LF FREQUENCY AXIS PEAKS: | 0 | 0 | 0 | 0 |
| LF TEMPORAL AXIS PEAKS: | 0 | 0 | 0 | 0 |
| SPECTRAL TURBULENCE: | 5 | 5 | 3 | |
| LATE POTENTIAL DURATION: | 5.7 | 4.8 | 5.9 | 1.8 |

HIGH POWER MAIN QRS REGION

| | LEAD X | LEAD Y | LEAD Z | X+Y+Z |
|---|---|---|---|---|
| REGION DURATION: (MSEC) | 70.0 | 76.0 | 84.0 | 80.0 |
| HF BIAXIAL PEAKS: | 6 | 9 | 8 | 6 |
| HF FREQUENCY AXIS PEAKS: | 38 | 63 | 60 | 43 |
| HF TEMPORAL AXIS PEAKS: | 75 | 113 | 105 | 91 |
| LF BIAXIAL PEAKS: | 0 | 0 | 0 | 0 |
| LF FREQUENCY AXIS PEAKS: | 0 | 0 | 0 | 0 |
| LF TEMPORAL AXIS PEAKS: | 0 | 0 | 0 | 0 |
| SPECTRAL TURBULENCE: | 7 | 13 | 13 | 6 |
| LATE POTENTIAL DURATION: | 10.1 | 22.5 | 23.8 | 9.8 |

INTERPRETATION:

FIGURE 5

"TRUE POSITIVE" PATIENT AT RISK

| PATIENT: | REPORT NO: 0687 | BEATS AVERAGED: 675 | SPECTROCARDIOGRAM™ | PARAMETERS: |
|---|---|---|---|---|
| AGE: SEX: | REPORT DATE: | SAMPLING FREQUENCY: 1000 HZ | TIME SLICE DURATION: | 24.0 MSEC |
| INDICATION: | TEST DATE 29.08.08 | FILE NAME: BERRY.R00 | TIME SLICE STEP INTERVAL: | 2.0 MSEC |
| PHYSICIAN: | SAMPLE TIME: 05:15 | | SIGNAL PRECONDITIONING: | VELOCITY |
| MEDICATION: | | | DC OFFSET SUBTRACTION: | PRE-WINDOW |
| COMMENT: | | | FFT POINTS: | 64 |
| | | | WINDOW: | BLACKMAN-HARRIS |

LEAD X                                    LEAD Y                                    LEAD Z                              X + Y + Z
TOTAL QRS DURATION: ( MSEC )166.0 | TOTAL QRS DURATION: ( MSEC )170.0 | TOTAL QRS DURATION: ( MSEC )140.0 | TOTAL QRS DURATION: ( MSEC )164.0

| | LEAD X | LEAD Y | LEAD Z | X+Y+Z |
|---|---|---|---|---|
| LOW POWER TERMINAL QRS REGION | | | | |
| PSD40: (MSEC) | 70.0 | 72.0 | 44.0 | 68.0 |
| HFQRS DURATION: | 1.8 | 0.6 | 3.0 | 1.1 |
| HF BIAXIAL PEAKS: | 5 | 7 | 5 | 5 |
| HF FREQUENCY AXIS PEAKS: | 40 | 41 | 28 | 35 |
| HF TEMPORAL AXIS PEAKS: | 69 | 59 | 56 | 56 |
| LF BIAXIAL PEAKS: | 0 | 0 | 0 | 0 |
| LF FREQUENCY AXIS PEAKS: | 0 | 0 | 0 | 0 |
| LF TEMPORAL AXIS PEAKS: | 0 | 0 | 0 | 0 |
| SPECTRAL TURBULANCE: | 18 | 26 | 12 | 13 |
| LATE POTENTIAL DURATION: | 33.0 | 47.0 | 18.3 | 21.0 |
| HIGH POWER MAIN QRS REGION | | | | |
| REGION DURATION: (MSEC) | 96.0 | 94.0 | 92.0 | 96.0 |
| HF BIAXIAL PEAKS: | 12 | 15 | 10 | 9 |
| HF FREQUENCY AXIS PEAKS: | 85 | 76 | 70 | 71 |
| HF TEMPORAL AXIS PEAKS: | 155 | 145 | 132 | 138 |
| LF BIAXIAL PEAKS: | 0 | 0 | 0 | 0 |
| LF FREQUENCY AXIS PEAKS: | 0 | 0 | 0 | 0 |
| LF TEMPORAL AXIS PEAKS: | 0 | 0 | 0 | 0 |
| SPECTRAL TURBULANCE: | 16 | 24 | 20 | 6 |
| LATE POTENTIAL DURATION: | 25.9 | 49.2 | 26.9 | 11.6 |

INTERPRETATION:

FIGURE 7